United States Patent
Oury et al.

(10) Patent No.: US 10,905,691 B2
(45) Date of Patent: Feb. 2, 2021

(54) USE OF TRIAZOLO(4,5-D)PYRIMIDINE DERIVATIVES FOR PREVENTION AND TREATMENT OF BACTERIAL INFECTION

(71) Applicant: Universite de Liege, Liege (BE)

(72) Inventors: Cécile Oury, Liege (BE); Patrizio Lancellotti, Liege (BE)

(73) Assignee: UNIVERSITÉ DE LIÈGE, Liege (BE)

( * ) Notice: Subject to any disclaimer, the term of this patent is extended or adjusted under 35 U.S.C. 154(b) by 0 days.

(21) Appl. No.: 16/688,961

(22) Filed: Nov. 19, 2019

(65) Prior Publication Data
US 2020/0093826 A1    Mar. 26, 2020

Related U.S. Application Data

(63) Continuation-in-part of application No. 16/331,920, filed as application No. PCT/EP2017/068811 on Jul. 25, 2017, now abandoned.

(30) Foreign Application Priority Data

Sep. 9, 2016 (EP) ..................... 16188201

(51) Int. Cl.
| A61K 31/519 | (2006.01) |
| C07D 487/04 | (2006.01) |
| A61P 31/04 | (2006.01) |
| A61L 2/00 | (2006.01) |
| A61L 2/16 | (2006.01) |

(52) U.S. Cl.
CPC .......... A61K 31/519 (2013.01); A61L 2/0082 (2013.01); A61L 2/16 (2013.01); A61P 31/04 (2018.01); *A61L 2202/24* (2013.01)

(58) Field of Classification Search
CPC .................... A61K 31/519; C07D 487/04
See application file for complete search history.

(56) References Cited

U.S. PATENT DOCUMENTS

| 6,251,910 B1 | 6/2001 | Guile et al. |
| 6,525,060 B1 | 2/2003 | Hardern et al. |
| 7,265,124 B2 | 9/2007 | Bohlin et al. |
| 8,802,850 B2 | 8/2014 | Rao et al. |
| 8,883,802 B2 | 11/2014 | Cosgrove et al. |
| 9,101,642 B2 | 8/2015 | Cosgrove et al. |
| 9,233,966 B2 | 1/2016 | Dahanukar et al. |
| 9,284,320 B2 | 3/2016 | Zupancic |

FOREIGN PATENT DOCUMENTS

| WO | WO 2000/34283 A1 | 6/2000 |
| WO | WO 2009/034386 A1 | 3/2009 |
| WO | WO 2013/092900 A1 | 6/2013 |
| WO | WO 2014/000719 A1 | 1/2014 |
| WO | WO 2015/014089 A1 | 2/2015 |
| WO | WO 2015/162537 A1 | 10/2015 |
| WO | WO 2016/116942 A1 | 7/2016 |

OTHER PUBLICATIONS

Alsharif et al., Ticagrelor Potentiates Adenosine-Induced Stimulation of Neutrophil Chemotaxis and Phagocytosis, Vascular Pharmacology, vol. 71, pp. 201-207 (Year: 2015).*
Kumar et al. 2016 "Four Process-Related Potential New Impurities in Ticagrelor: Identification, Isolation, Characterization Using HPLC, LC/ESI-MS.sup.n, NMR and Their Synthesis" *Journal of Pharmaceutical and Biomedical Analysis* 120: 248-260.
IPCOM000234711D, 2014 "Impurities of (1S,2S,3R,5S)-3-[7-[[(1R,2S)-2-(3,4-difluorophenyl)cyclopropyl]amino]-5-(propylthio)-3H-1,2,3-triazolo[4,5,d]pyrimidine-3-yl]-5-(2-hydroxyethoxy)-1,2-cyclopentanediol", on the internet at: ip.com/IPCOM000234711.
Radzishevsky, I. et al. 2007 "Antiplasmodial Activity of Lauryl-Lysine Oligomers" *Angimicrobial Agents and Chemotherapy* 51: 1753-1759.

* cited by examiner

*Primary Examiner* — Brenda L Coleman
(74) *Attorney, Agent, or Firm* — Knobbe, Martens, Olson & Bear, LLP

(57) ABSTRACT

A method for treatment of a bacterial infection in a host mammal in need of such treatment or a method of administering to the host mammal an effective amount of a Triazolo(4,5-d)pyrimidine of formula(I):

(I)

wherein $R^1$ is $C_{3-5}$ alkyl optionally substituted by one or more halogen atoms; $R^2$ is a phenyl group, optionally substituted by one or more halogen atoms; $R^3$ and $R^4$ are both hydroxyl; R is XOH, wherein X is $CH_2$, $OCH_2CH_2$, or a bond, and wherein when X is a bond, R is OH; or a pharmaceutical acceptable salt, provided that when X is $CH_2$ or a bond, $R^1$ is not propyl; when X is $CH_2$ and $R^1$ is $CH_2CH_2CF_3$, butyl or pentyl, the phenyl group at $R^2$ must be substituted by fluorine; when X is $OCH_2CH_2$ and $R^1$ is propyl, the phenyl group at $R^2$ must be substituted by fluorine.

20 Claims, 17 Drawing Sheets

C

A

B

USE OF TRIAZOLO(4,5-D)PYRIMIDINE DERIVATIVES FOR PREVENTION AND TREATMENT OF BACTERIAL INFECTION

FIELD

The present invention relates to a new use of Triazolo(4,5-d)pyrimidine derivatives for prevention and treatment of bacterial infection.

BACKGROUND

Bacteria are often incriminated in healthcare-associated infections (including medical device-related infections), causing increased patient morbidity and mortality, and posing huge financial burden on healthcare services. The situation has become critical since more and more bacteria are becoming resistant to antibiotics belonging to various classes such as Penicillins, Methicillins, Carbapenems, Cephalosporins, Quinolones, Amino-glycosides, and Glycopeptides, and an increasing number of infections are becoming difficult to cure.

The increasing resistance to antibiotics is a growing public health concern because of the limited treatment options available for these serious infections. In Europe, antimicrobial resistance causes approximately 25,000 deaths every year. The clinical burden associated with antimicrobial resistance is estimated to cost approximately €1.5 billion per year.

At present, 700,000 deaths are estimated to be attributed to antimicrobial resistance globally as reported in Review on AMR, Antimicrobial resistance: Tackling a crisis for the health and wealth of nations, 2014

The use of antibiotics is not safe especially in long-term therapy or high dose therapy. Such environmental pressure may promote selection of resistant bacteria, population, altering population structure and increasing the risk of horizontal gene transfer leading to the mobility of resistant genes into the microbiome.

Antibiotic treatment targets both the «good» and the «bad» bacteria.

The human gastro-intestinal tract (GI) microbiota is made of about trillions of microorganisms most of them bacteria. Microbiota and host's defense relationship is essential for metabolic and physiological functions contributing to health. By disrupting this benefit interaction, dietary components, physical and psychological stress, drugs but also antibiotics increase incidence of several diseases like obesity, inflammation and cardiovascular diseases (CVD). CVD remain the first cause of death in industrial society with growing incidence in other countries.

For instance recent studies showed a direct link between long term antibiotics treatment, disruption of GI microbiota and risks of atherosclerosis in mice.

The source of bacterial infection is diverse and there is a large number of bacterial infections.

Infections caused by Gram-positive bacteria represent a major public health burden, not just in terms of morbidity and mortality, but also in terms of increased expenditure on patient management and implementation of infection control measures. *Staphylococcus aureus* and enterococci are established pathogens in the hospital environment, and their frequent multidrug resistance complicates therapy.

*Staphylococcus aureus* is an important pathogen responsible for a broad range of clinical manifestations ranging from relatively benign skin infections to life-threatening conditions such as endocarditis and osteomyelitis. It is also a commensal bacterium (colonizing approximately 30 percent of the human population).

Two major shifts in *S. aureus* epidemiology have occurred since the 1990s: an epidemic of community-associated skin and soft tissue infections (largely driven by specific methicillin-resistant *S. aureus* [MRSA] strains), and an increase in the number of healthcare-associated infections (especially infective endocarditis and prosthetic device infections).

Coagulase-negative staphylococci (CoNS) are the most frequent constituent of the normal flora of the skin. These organisms are common contaminants in clinical specimens as well as increasingly recognized as agents of clinically significant infection, including bacteremia and endocarditis. Patients at particular risk for CoNS infection include those with prosthetic devices, pacemakers, intravascular catheters, and immunocompromised hosts.

Coagulase-negative staphylococci account for approximately one-third of bloodstream isolates in intensive care units, making these organisms the most common cause of nosocomial bloodstream infection.

Enterococcal species can cause a variety of infections, including urinary tract infections, bacteremia, endocarditis, and meningitis. Enterococci are relatively resistant to the killing effects of cell wall-active agents (penicillin, ampicillin, and vancomycin) and are impermeable to aminoglycosides.

Vancomycin-resistant enterococci (VRE) are an increasingly common and difficult-to-treat cause of hospital-acquired infection.

Multiple epidemics of VRE infection have been described in diverse hospital settings (e.g., medical and surgical intensive care units, and medical and pediatric wards) and, like methicillin-resistant *Staphylococcus aureus*, VRE is endemic in many large hospitals. The beta-hemolytic *Streptococcus agalactiae* (Group B *Streptococcus*, GBS) is another Gram-positive bacteria. The bacteria can cause sepsis and/or meningitis in the newborn infants. It is also an important cause of morbidity and mortality in the elderly and in immuno-compromised adults. Complications of infection include sepsis, pneumonia, osteomyelitis, endocarditis, and urinary tract infections.

The factors that make these bacteria especially adept at surviving on various biomaterials include adherence and production of biofilm (see below).

The four above mentioned bacteria have the ability to form biofilms on any surface biotic and abiotic. The initial step of biofilm formation is the attachment/adherence to surface, which is stronger in shear stress conditions. The protein mainly responsible for this adhesion is the polysaccharide intercellular adhesin (PIA), which allows bacteria to bind to each other, as well as to surfaces, creating the biofilm. The second stage of biofilm formation is the development of a community structure and ecosystem, which gives rise to the mature biofilm. The final stage is the detachment from the surface with consequent spreading into other locations. In all the phases of biofilm formation the quorum sensing (QS) system, mediating cell-to-cell communication, is involved.

Bacteria in the biofilm produce extracellular polymeric substances (EPS) consisting mainly of polysaccharides, nucleic acids (extracellular DNA) and proteins, that protect them from external threats, including immune system components and antimicrobials. Moreover, bacteria in the biofilm have a decreased metabolism, making them less susceptible to antibiotics; this is due to the fact that most antimicrobials require a certain degree of cellular activity in order to be effective. Another factor reinforcing such resistance is the impaired diffusion of the antibiotics throughout the biofilm because of the presence of the EPS matrix barrier.

It was also reported that in the biofilm there is higher rate of plasmid exchange increasing the chances of developing naturally occurring and antimicrobial-induced resistance.

Strategies that have been developed to eliminate biofilms target 3 different steps in the biofilm formation: inhibition of the initial stage, i.e. the adhesion of bacteria to surfaces; disrupting the biofilm architecture during the maturation process or step 2; inhibiting the QS system or step 3.

Because of the high resistance of these biofilms to antibiotics there is an increasing need of control and prevention of microbial growth and biofilm formation at step 2. The treatment in case of infected medical device is either a conservative treatment or the removal of the device together with a long treatment with antibiotics, but these approaches have high failure rates and elevated economical burden.

This is the reason why clinicians try to adopt a preventive approach by subministering antibiotics before implantation. Another solution could be the modification of the medical devices, e.g. surfaces coated with silver, which have antimicrobial property or with hydrogels as well as polyurethanes, which reduce bacterial adhesion, to mention few examples.

According to Eggiman in American Society for Microbiology Press, Washington, D.C. 2000. p. 247, pacemakers and implantable cardioverter-defibrillators [ICDs]) can become infected, with a rate of infections ranging from 0.8 to 5.7 percent.

The infection can involve subcutaneous pocket containing the device or the subcutaneous segment of the leads. Deeper infection can also occur that involves the transvenous portion of the lead, usually with associated bacteremia and/or endovascular infection.

The device and/or pocket itself can be the source of infection, usually due to contamination at the time of implantation, or can be secondary to bacteremia from a different source.

Perioperative contamination of the pacemaker pocket with skin flora appears to be the most common source of subcutaneous infection.

Cardiac device-related infective endocarditis (CDRIE) is another life-threatening condition, with increasing incidence due to growing number of implantations (81000 pacemaker implantation per year in Europe). The incidence of CDRIE reaches 0.14 percent, and is even higher after ICD implantation.

*Staphylococcus aureus* and coagulase-negative staphylococci (often *Staphylococcus epidermidis*) cause 65 to 75 percent of generator pocket infections and up to 89 percent of device-related endocarditis. Episodes arising within two weeks of implantation are more likely to be due to *S. aureus*.

Successful treatment of an infected medical device or biomaterial, regardless of the involved component, generally requires removal of the entire system and administration of antibiotics targeting the causative bacteria. Importantly, medical therapy alone is associated with high mortality and risk of recurrence.

Prosthetic valve endocarditis (PVE) is a serious infection with potentially fatal consequences.

Bacteria can reach the valve prosthesis by direct contamination intraoperatively or via hematogenous spread during the initial days and weeks after surgery. The bacteria have direct access to the prosthesis-annulus interface and to perivalvular tissue along suture pathways because the valve sewing ring, cardiac annulus, and anchoring sutures are not endothelialized early after valve implantation. These structures are coated with host proteins, such as fibronectin and fibrinogen, to which some organisms can adhere and initiate infection.

The risk of developing prosthetic valve endocarditis (PVE) is greatest during the initial three months after surgery, remains high through the sixth month, and then falls gradually with an annual rate of approximately 0.4 percent from 12 months postoperatively onward. The percentage of patients developing PVE during the initial year after valve replacement ranges from 1 to 3 percent in studies with active follow-up; by five years, the cumulative percentage ranges from 3 to 6 percent.

The most frequently encountered pathogens in early PVE (within two months of implantation) are *S. aureus* and coagulase-negative staphylococci.

The most frequently encountered pathogens in late PVE (two months after valve implantation) are streptococci and *S. aureus*, followed by coagulase-negative staphylococci and enterococci.

The coagulase-negative staphylococci causing PVE during the initial year after surgery are almost exclusively *Staphylococcus epidermidis*. Between 84 and 87 percent of these organisms are methicillin resistant and thus resistant to all of the beta-lactam antibiotics.

According to the 2008 French survey, PVE accounts for about 20 percent of all infective endocarditis. PVE is related to health care in about 30 percent of cases. *S. aureus* is the first causative pathogen, being responsible for more than 20 percent of PVE. Importantly, when comparing data from 1999, PVE-related mortality remains high, reaching about 40 percent after surgery, and 25 percent in-hospital mortality.

Periprosthetic joint infection (PJI) occurs in 1 to 2 percent of joint replacement surgeries and is a leading cause of arthroplasty failure.

Biofilms play an important role in the pathogenesis of PJIs. Bacteria within biofilm become resistant to therapy; as a result, antibacterial therapy is often unsuccessful unless the biofilm is physically disrupted or removed by surgical debridement.

Prosthetic joint infections are categorized according to the timing of symptom onset after implantation: early onset (<3 months after surgery), delayed onset (from 3 to 12 months after surgery), and late onset (>12 months after surgery). These infections have the following characteristics. Early-onset infections are usually acquired during implantation and are often due to virulent organisms, such as *Staphylococcus aureus*, or mixed infections. Delayed-onset infections are also usually acquired during implantation. Consistent with the indolent presentation, delayed infections are usually caused by less virulent bacteria, such as coagulase-negative staphylococci or enterococci. Late-onset infections resulting from hematogenous seeding are typically acute and often due to *S. aureus*, or beta hemolytic streptococci.

The management of PJIs generally consists of both surgery and antibacterial therapy.

There is therefore an urgent need in the art for a new antibacterial therapy.

We have surprisingly found that Triazolo(4,5-d)pyrimidine derivatives possess antibacterial activity and can be used in the treatment or prevention of bacterial infection in a host mammal.

We have also found that such Triazolo(4,5-d)pyrimidine derivatives can also be used in a method for controlling bacterial growth in biofilm formation at early stage such as step 1 or 2 or for killing bacteria at all steps of biofilm formation including the latest step 3 wherein the biofilm has reached its maturation stage of matrix formation and start detachment from the surface with a consequent spreading of bacteria into other locations.

In a first aspect, the invention provides therefore Triazolo (4,5-d)pyrimidine derivatives for use in the treatment or prevention of bacterial infection in a host mammal in need of such treatment.

By bacterial infection one means particularly Gram-positive bacterial infection such as for example pneumonia, septicemia, endocarditis, osteomyelitis, meningitis, urinary tract, skin, and soft tissue infections. The source of bacterial infection is diverse, and can be caused for example by the use of implantable biomaterials. By bacterial infection, one also means Gram-negative bacterial infection.

By prevention of bacterial infection, it is intended to refer to a reduction in risk of acquiring infection, or reduction or inhibition of recurrence of infection. For example, the Triazolo(4,5d)pyrimidine derivatives may be administered as prevention before a surgical treatment to prevent infection or after a bite or wound that could get infected or in case of health problem such as cancer and chemotherapy treatment or sickle cell anaemia.

The term "Gram-negative bacteria" as used herein corresponds to the term in as known in the art, i.e. bacteria characterized by an envelope consisting of 3 main layers, i.e. an outer membrane containing lipopolysaccharides (LPS), a peptidoglycan cell wall with peptide chains that are generally cross-linked and a cytoplasmic or inner membrane, also called integral membrane protein. In particular embodiments, the gram-negative bacteria is for example *Acinetobacter* spp., such as *Acinetobacter baumannii*, *Bordetella pertussis*, *Campylobacter* spp.; Enterobacteriaceae such as *Citrobacter* spp., *Enterobacter* spp., *Escherichia coli*, *Klebsiella* spp., *Salmonella* spp., *Serratia marcescens*, *Shigella* spp., *Yersinia* spp.; *Haemophilus influenza*, *Helocobacter pylorilegionella pneumophila*, *Neisseria* spp., *Pseudomonas aeruginosa*, *Vibrio cholera* and the like.

In particular embodiments, the "Gram-negative bacteria" are resistant to one or more commonly used antibiotics including quinolones (such as ciprofloxacin), colistins (polymyxins), carbapenems (such as imipenem, meropenem), cephalosporins (such as cefotaxime, ceftazidime), and other β-lactam antibiotics and the like.

Besides humans, companion animals, such as cats, dogs, and horses, can also be colonized and infected by Gram-negative bacteria, without host adaptation, and therefore may act as reservoirs for human infections. Bacteria can also develop distinct resistance when hosted by animals. Antibiotic use in agriculture (for example inappropriate uses of antibiotics in food animals and other aspects of agriculture and aquaculture) contributes to the emergence of resistant bacteria and their spread to humans.

The term "membrane penetrating agent" as used herein refers to a molecule able to penetrate through the outer membrane of a Gram-negative bacteria. It is for example a small hydrophilic molecule such as a β-lactam that use the pores formed by porins to gain access inside to the bacteria or an hydrophobic molecule that diffuse across the outer membrane layer.

Preferred membrane penetrating agents include but are not limited to polymyxin, polymyxin derivatives, aminoglycosides, dibasic macrolides, oligo-acyl-lysyls (OAKS) or cationic peptides such as for example dilipid ultrashort cationic lipopeptides.

Polymyxins are for example Polymyxin B (PMB) and Polymyxin E (also called colistin). Polymyxins are cyclic lipodecapeptide and have five free amino groups (di-aminobutyric acid residues) and a C8-C9 fatty acid side chain as illustrated in formula (VII). Polymyxins are therefore both cationic and lipophilic.

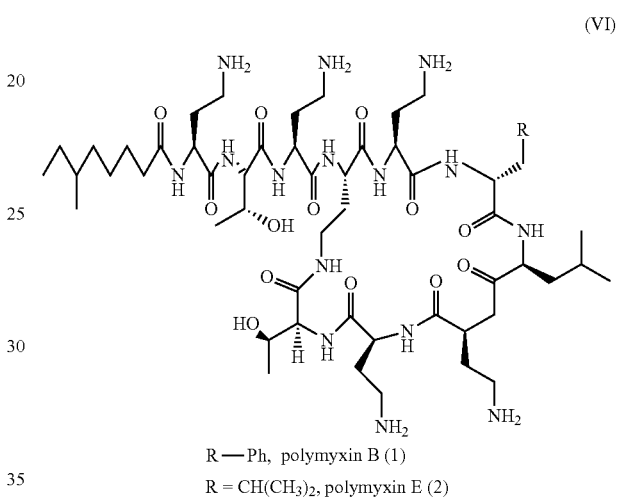

R—Ph, polymyxin B (1)
R = CH(CH3)2, polymyxin E (2)

Polymyxin derivatives are for example polymyxin B nonapeptide (PMBN) wherein the fatty acyl tail and N-terminal diaminobutyryl (Dab) residue of polymyxin B are lacking, as illustrated in formula (VII):

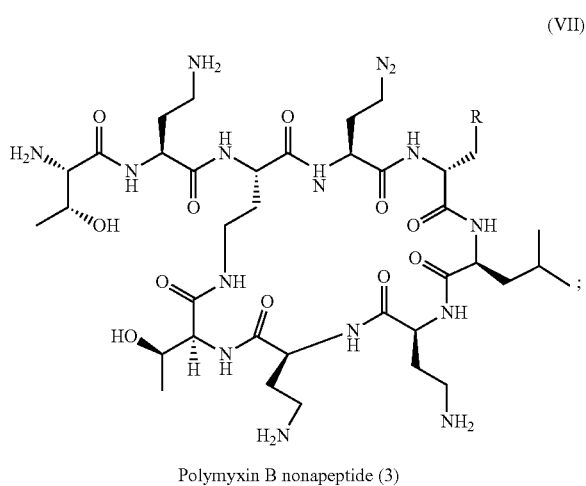

Polymyxin B nonapeptide (3)

or polymyxin B derivatives wherein a DAB residue (di-aminobutyryl residue) of the linear chain of polymyxin has been replaced by an aminobutyric acid or serine as illustrated in formula (VIII) and formula (IX) respectively:

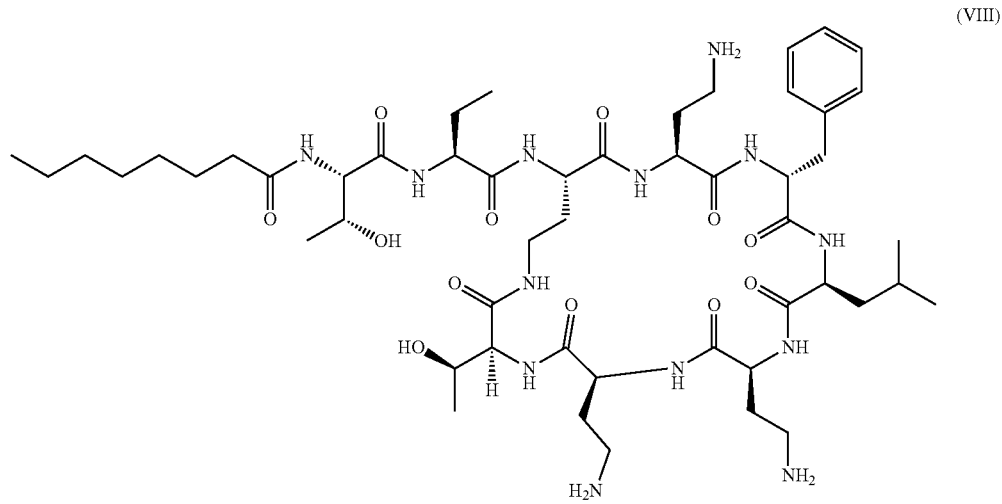
(VIII)
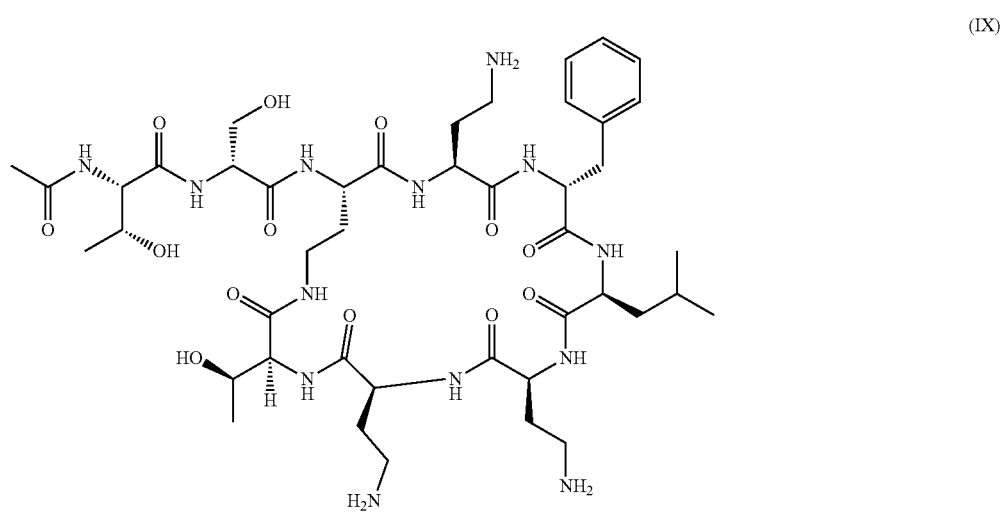
(IX)
Polymyxin derivatives corresponding to formula (VIII) and (IX) are also respectively called SPR7061 and SPR741 in the art.
Oligo-acyl-lysyls (OAKS) are peptides with acyl chains alternating with cationic amino acids, such as lysine, histidine and arginine; as illustrated in formula (X).
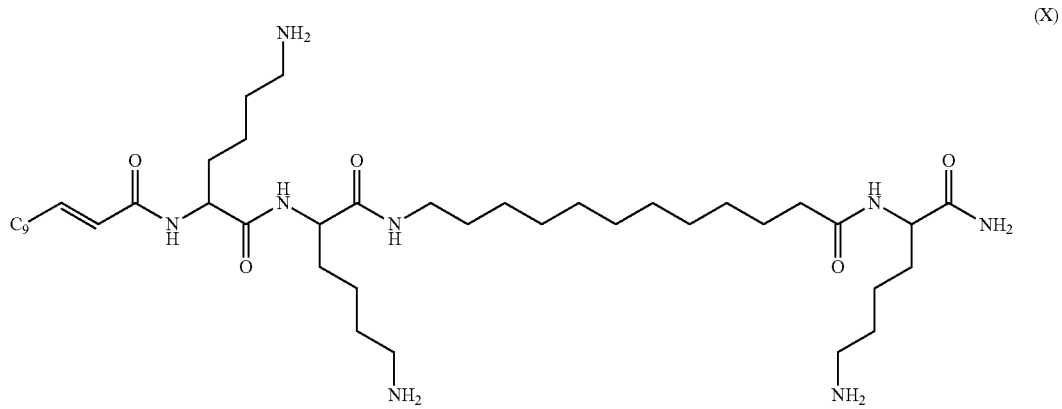
(X)
OAK C12(☒7)X Preferred oligo-acyl-lysyl is C12(ω7)K-β12 wherein ω7 indicates the presence and position of a double bond in C12 chain and β12 represents a sequence of lysyl-aminododecanoyl-lysyl as illustrated in formula (XI):

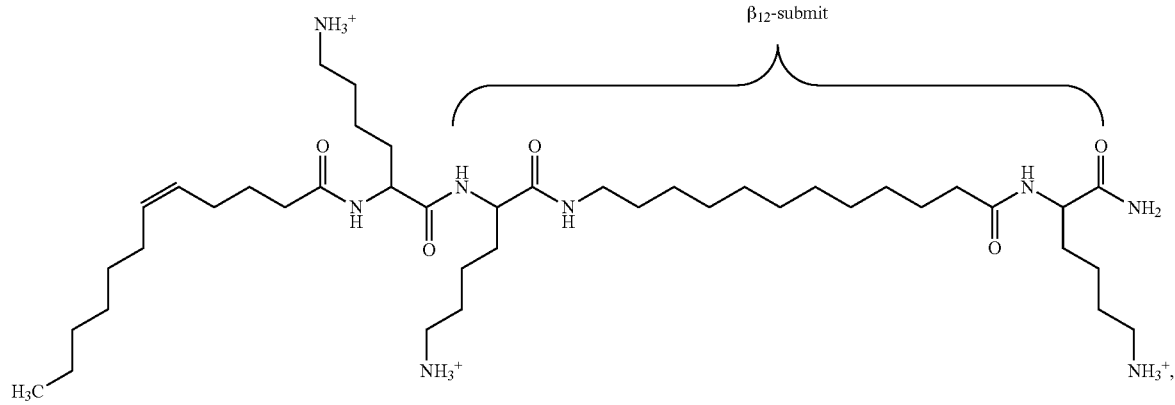

By biomaterials, one means all implantable foreign material for clinical use in host mammals such as for prosthetic joints, pacemakers, implantable cardioverter

SUMMARY

Some aspects relate to a method for treatment of a bacterial infection in a host mammal in need of such treatment or a method of administering to the host mammal an effective amount of a Triazolo(4,5-d)pyrimidine of formula(I):

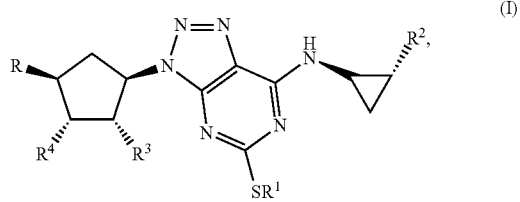

wherein $R^1$ is $C_{3-5}$ alkyl optionally substituted by one or more halogen atoms; $R^2$ is a phenyl group, optionally substituted by one or more halogen atoms; $R^3$ and $R^4$ are both hydroxyl; R is XOH, wherein X is $CH_2$, $OCH_2CH_2$, or a bond, and wherein when X is a bond, R is OH;
or a pharmaceutical acceptable salt, provided that when X is $CH_2$ or a bond, $R^1$ is not propyl; when X is $CH_2$ and $R^1$ is $CH_2CH_2CF_3$, butyl or pentyl, the phenyl group at $R^2$ must be substituted by fluorine; when X is $OCH_2CH_2$ and $R^1$ is propyl, the phenyl group at $R^2$ must be substituted by fluorine.

In some examples, $R^2$ is phenyl substituted by fluorine atoms.

In some examples, R is OH or $OCH_2CH_2OH$.

In some examples, R is OH.

In some examples, the Triazolo(4,5-d)pyrimidine of formula(I) is selected from the group consisting of:
(1R-(1α, 2α, 3β(1R*, 2*),5β))-3-(7-((2-(3,4-difluorophenyl) cyclopropyl)amino)-5-((3,3,3-trifluoropropyl)thio)3H-1, 2,3-triazolo(4,5d)pyrimidin-3 yl)5(hydroxy)cyclopentane-1,2-diol;
(1S-(1α, 2α, 3β(1R*, 2*),5β))-3-(7-((2-(3,4-difluorophenyl)cyclopropyl)amino)-5-(propylthio)-3H-1,2,3-triazolo (4,5d)pyrimidin-3-yl)5(2-hydroxyethoxy)cyclopentane-1,2-diol;
(1S,2S,3R,5S)-3-[7-[(1R,2S)-2-(3,4-difluorophenyl)cyclopropylamino]-5-(propylthio)-3H-[1,2,3]-triazolo[4,5-d] pyrimidin-3-yl]-5-(2-hydroxyethoxy)-1,2-cyclopentanediol;
(1S,2S,3R,5S)-3-[7-[(1R,2S)-2-(4-fluorophenyl)cyclopropylamino]-5-(propylthio)-3H-[1,2,3]-triazolo[4,5-d]pyrimidin-3-yl]-5-(2-hydroxyethoxy)-1,2-cyclopentanediol;
(1S,2R,3S,4R)-4-[7-[[(1R,2S)-2-(3,4-Difluorophenyl)cyclopropyl]amino]-5-(propylthio)-3H-1,2,3-triazolo[4,5-d]pyrimidin-3-y]-1,2-3cyclopentanetriol; and
a pharmaceutical acceptable salt.

In some examples, the Triazolo(4,5-d)pyrimidine of formula(I) is (1S,2S,3R,5S)-3-[7-[(1R,2S)-2-(3,4-difluorophenyl)cyclopropylamino]-5-(propylthio)-3H-[1,2,3]-triazolo [4,5-d]pyrimidin-3-yl]-5-(2-hydroxyethoxy)-1,2-cyclopentanediol, also called Triafluocyl.

In some examples, the Triazolo(4,5-d)pyrimidine is (1R, 2R,3S,4R)-4-[7-[[(1R,2S)-2-(3,4-Difluorophenyl)cyclopropyl]amino]-5-(propylthio)-3H-1,2,3-triazolo[4,5-d]pyrimidin-3-yl]-1,2,3-cyclopentanetriol, also called Fluometacyl.

In some examples, the effective amount to be administered to the host mammal is less than 1.8 g per day.

Some aspects relate to a method of killing bacteria or reducing bacterial growth in a biofilm formation comprising applying on a surface an effective amount of a Triazolo(4, 5-d)pyrimidine of formula (I):

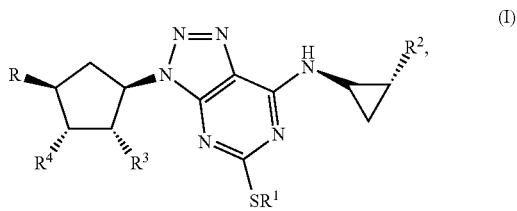

wherein $R^1$ is $C_{3-5}$ alkyl optionally substituted by one or more halogen atoms; $R^2$ is a phenyl group, optionally substituted by one or more halogen atoms; R3 and R4 are both hydroxyl; R is XOH, wherein X is $CH_2$, $OCH_2CH_2$, or a bond, and wherein when X is a bond, R is OH;

or a pharmaceutical acceptable salt, provided that when X is $CH_2$ or a bond, $R^1$ is not propyl; when X is $CH_2$ and $R^1$ is $CH_2CH_2CF_3$, butyl or pentyl, the phenyl group at $R^2$ must be substituted by fluorine; when X is $OCH_2CH_2$ and $R^1$ is propyl, the phenyl group at $R^2$ must be substituted by fluorine.

In some examples, $R^2$ is phenyl substituted by fluorine atoms.

In some examples, R is OH or $OCH_2CH_2OH$.

In some examples, R is OH.

In some examples, the Triazolo(4,5-d)pyrimidine derivative of formula(I) is selected from the group consisting of:
(IR-(1α, 2α, 3β(1R*, 2*),5β))-3-(7-((2-(3,4-difluorophenyl)cyclopropyl)amino)-5-((3,3,3-trifluoropropyl)thio)3H-1,2,3-triazolo(4,5d)pyrimidin-3 yl)5(hydroxy)cyclopentane-1,2-diol;
(1S-(1α, 2α, 3β(1R*, 2*),5β))-3-(7-((2-(3,4-difluorophenyl)cyclopropyl)amino)-5-(propylthio)-3H-1,2,3-triazolo(4,5d)pyrimidin-3-yl)5(2-hydroxyethoxy)cyclopentane-1,2-diol;
(1S,2S,3R,5S)-3-[7-[(1R,2S)-2-(3,4-difluorophenyl)cyclopropylamino]-5-(propylthio)-3H-[1,2,3]-triazolo[4,5-d]pyrimidin-3-yl]-5-(2-hydroxyethoxy)-1,2-cyclopentanediol;
(1S,2S,3R,5S)-3-[7-[(1R,2S)-2-(4-fluorophenyl)cyclopropylamino]-5-(propylthio)-3H-[1,2,3]-triazolo[4,5-d]pyrimidin-3-yl]-5-(2-hydroxyethoxy)-1,2-cyclopentanediol;
(1S,2R,3S,4R)-4-[7-[[(1R,2S)-2-(3,4-Difluorophenyl)cyclopropyl]amino]-5-(propylthio)-3H-1,2,3-triazolo[4,5-d]pyrimidin-3-y]-1,2-3cyclopentanetriol; and
a pharmaceutical acceptable salt.

In some examples, the Triazolo(4,5-d)pyrimidine derivative of formula(I) is (1S,2S,3R,5S)-3-[7-[(1R,2S)-2-(3,4-difluorophenyl)cyclopropylamino]-5-(propylthio)-3H-[1,2,3]-triazolo[4,5-d]pyrimidin-3-yl]-5-(2-hydroxyethoxy)-1,2-cyclopentanediol, also called Triafluocyl.

In some examples, the Triazolo(4,5-d)pyrimidine is (1S,2R,3S,4R)-4-[7-[[(1R,2S)-2-(3,4-Difluorophenyl)cyclopropyl]amino]-5-(propylthio)-3H-1,2,3-triazolo[4,5-d]pyrimidin-3-yl]-1,2,3-cyclopentanetriol, also called Fluometacyl.

In some examples, the effective amount is between 0.1 and 1000 µg/ml.

In some examples, the surface is located on a medical device.

In some examples, the surface is located on a biomaterial.
In some examples, the medical device is a heart valve.
In some examples, the medical device is a catheter.

Some aspects relate to a method of reducing risk of acquiring a bacterial infection in a host mammal comprising administering to the host mammal an effective amount of a Triazolo(4,5-d)pyrimidine of formula(I):

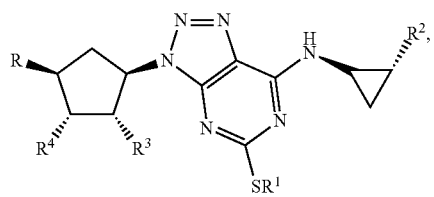

wherein $R^1$ is $C_{3-5}$ alkyl optionally substituted by one or more halogen atoms; $R^2$ is a phenyl group, optionally substituted by one or more halogen atoms; R3 and R4 are both hydroxyl; R is XOH, wherein X is $CH_2$, $OCH_2CH_2$, or a bond, and wherein when X is a bond, R is OH;

or a pharmaceutical acceptable salt, provided that when X is $CH_2$ or a bond, $R^1$ is not propyl; when X is $CH_2$ and $R^1$ is $CH_2CH_2CF_3$, butyl or pentyl, the phenyl group at $R^2$ must be substituted by fluorine; when X is $OCH_2CH_2$ and $R^1$ is propyl, the phenyl group at $R^2$ must be substituted by fluorine.

In some examples, the Triazolo(4,5-d)pyrimidine of formula(I) is (1S,2S,3R,5S)-3-[7-[(1R,2S)-2-(3,4-difluorophenyl)cyclopropylamino]-5-(propylthio)-3H-[1,2,3]-triazolo[4,5-d]pyrimidin-3-yl]-5-(2-hydroxyethoxy)-1,2-cyclopentanediol, also called Triafluocyl.

In some examples, the Triazolo(4,5-d)pyrimidine is (1S,2R,3S,4R)-4-[7-[[(1R,2S)-2-(3,4-Difluorophenyl)cyclopropyl]amino]-5-(propylthio)-3H-1,2,3-triazolo[4,5-d]pyrimidin-3-yl]-1,2,3-cyclopentanetriol, also called Fluometacyl.

We have surprisingly found that Triazolo(4,5-d)pyrimidine derivatives possess antibacterial activity and can be used in the treatment or prevention of bacterial infection in a host mammal.

We have also found that such Triazolo(4,5-d)pyrimidine derivatives can also be used in a method for controlling bacterial growth in biofilm formation at early stage such as step 1 or 2 or for killing bacteria at all steps of biofilm formation including the latest step 3 wherein the biofilm has reached its maturation stage of matrix formation and start detachment from the surface with a consequent spreading of bacteria into other locations.

In a first aspect, the invention provides therefore Triazolo(4,5-d)pyrimidine derivatives for use in the treatment or prevention of bacterial infection in a host mammal in need of such treatment.

By bacterial infection one means particularly Gram-positive bacterial infection such as for example pneumonia, septicemia, endocarditis, osteomyelitis, meningitis, urinary tract, skin, and soft tissue infections. The source of bacterial infection is diverse, and can be caused for example by the use of implantable biomaterials.

By biomaterials, one means all implantable foreign material for clinical use in host mammals such as for prosthetic joints, pacemakers, implantable cardioverter-defibrillators, intravascular catheters, coronary stent, prosthetic heart valves, intraocular lens, dental implants and the like.

By Triazolo(4,5-d)pyrimidine derivatives one means compounds of the following formula (I)

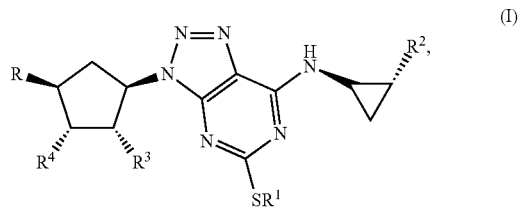

wherein R1 is C3-5 alkyl optionally substituted by one or more halogen atoms; $R_2$ is a phenyl group, optionally substituted by one or more halogen atoms; $R_3$ and $R_4$ are both hydroxyl; R is OH or XOH, wherein X is $CH_2$, $OCH_2CH_2$, or a bond;

or a pharmaceutical acceptable salt or solvate thereof, or a solvate thereof or a solvate of such a salt provided that when X is $CH_2$ or a bond, $R_1$ is not propyl; when X is $CH_2$ and $R_1$ $CH_2CH_2CF_3$, butyl or pentyl, the phenyl group at $R_2$ must be substituted by fluorine; when X is OCH$_2$CH$_2$ and R$_1$ is propyl, the phenyl group at R$_2$ must be substituted by fluorine.

Alkyl groups whether alone or as part of another group are straight chained and fully saturated.

R$_1$ is a C$_{3-5}$ alkyl optionally substituted by one or more fluorine atoms. Preferably R$_1$ is 3,3,3,-trifluoropropyl, butyl or propyl.

R$_2$ is phenyl or phenyl substituted by one or more halogen atoms. Preferably R$_2$ is phenyl substituted by fluorine atoms. Most preferably R$_2$ is 4-fluorophenyl or 3,4-difluorophenyl.

R is OH or XOH, where X is CH$_2$, OCH$_2$CH$_2$, or a bond; preferably R is OH or OCH$_2$CH2OH. When X is a bond, R is OH.

Most preferred Triazolo(4,5-d)pyrimidine derivatives are the ones including R2 as 4-fluorophenyl or 3,4-difluorophenyl and or R as OCH$_2$CH$_2$OH.

Triazolo(4,5-d)pyrimidine derivatives are well known compounds. They may be obtained according to the method described in U.S. Pat. No. 6,525,060 which is incorporated by reference.

Triazolo(4,5-d)pyrimidine derivatives are used as medicament against platelet adhesion and aggregation that are primary steps in arterial thrombosis.

They work by antagonizing the platelet P2Y12 receptor for ADP in a reversible manner, providing antiplatelet effects after oral administration. P2Y12 is one of the two ADP receptors expressed by platelets, acting by amplifying platelet responses to other agonists, which stabilizes platelet aggregates and promotes thrombosis. As a consequence, P2Y12 inhibitors, alone or in combination with aspirin, significantly improve outcomes of patients with coronary artery disease and peripheral vascular disease.

We have now surprisingly found that such Triazolo(4,5-d)pyrimidine derivatives have also an antibacterial effect.

Preferred Triazolo(4,5-d)pyrimidine derivatives are derivatives with R equals OH or OCH$_2$CH2OH and/or R$_2$ equals 4-fluorophenyl or 3,4 difluorophenyl.

Most preferred Triazolo(4,5-d)pyrimidine derivatives are (1R-(1α, 2α, 3β(1R*, 2*),5β))-3-(7-((2-(3,4-difluorophenyl)cyclopropyl)amino)-5-((3,3,3-trifluoropropyl)thio)3H-1,2,3-triazolo(4,5d)pyrimidin-3-yl)5(hydroxy)cyclopentane-1,2-diol;

(1S-(1α, 2α, 3β(1R*, 2*),5β))-3-(7-((2-(3,4-difluorophenyl)cyclopropyl)amino)-5-(propylthio)(3H-1,2,3-triazolo(4,5d)pyrimidin-3-yl)5(2-hydroxyethoxy)cyclopentane-1,2-diol;

(1S,2S,3R,5S)-3-[7-[(1R,2S)-2-(3,4-difluorophenyl)cyclopropylamino]-5-(propylthio)-3H-[1,2,3]-triazolo[4,5-d]pyrimidin-3-yl]-5-(2-hydroxyethoxy)-1,2-cyclopentanediol);

(1S,2S,3R,5S)-3-[7-[(1R,2S)-2-(4-fluorophenyl)cyclopropylamino]-5-(propylthio)-3H-[1,2,3]-triazolo[4,5-d]pyrimidin-3-yl]-5-(2-hydroxyethoxy)-1,2-cyclopentanediol);

(1S,2R,3S,4R)-4-[7-[[(1R,2S)-2-(3,4-Difluorophenyl)cyclopropyl]amino]-5-(propylthio)-3H-1,2,3-triazolo[4,5-d]pyrimidin-3-yl]-1,2,3-cyclopentanetriol;

and pharmaceutical acceptable salt or solvate thereof, or a solvate thereof or a solvate of such a salt.

The most preferred Triazolo(4,5-d)pyrimidine derivative is (1S,2S,3R,5S)-3-[7-[(1R,2S)-2-(3,4-difluorophenyl)cyclopropylamino]-5-(propylthio)-3H-[1,2,3]-triazolo[4,5-d]pyrimidin-3-yl]-5-(2-hydroxyethoxy)-1,2-cyclopentanediol) as defined in formula (II) and also called Triafluocyl hereafter.

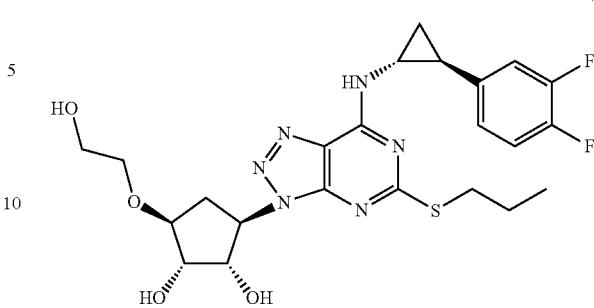

(II)

and a pharmaceutical acceptable salt or solvate thereof, or a solvate thereof or a solvate of such a salt.

Another most preferred Triazolo(4,5-d)pyrimidine derivative is (1S,2R,3S,4R)-4-[7-[[(1R,2S)-2-(3,4-Difluorophenyl)cyclopropyl]amino]-5-(propylthio)-3H-1,2,3-triazolo[4,5-d]pyrimidin-3-yl]-1,2,3-cyclopentanetriol as defined in formula (III) and also called Fluometacyl hereafter

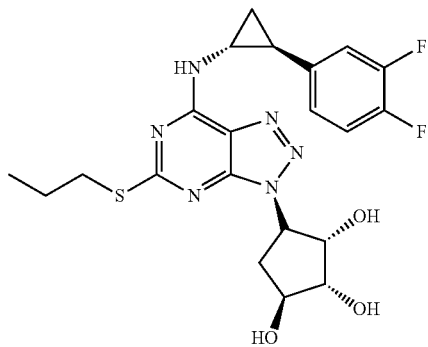

(III)

and a pharmaceutical acceptable salt or solvate thereof, or a solvate thereof or a solvate of such a salt.

According to the invention the Triazolo(4,5-d)pyrimidine derivative has to be administered to the patient over several days (especially in case of prevention). The Triazolo(4,5-d) pyrimidine derivative may be administered on their own or as a pharmaceutical composition, with non-toxic doses being inferior to 1.8 g per day.

A further preferred object of the invention is a pharmaceutical composition of Triazolo(4,5-d)pyrimidine derivative for use in the prevention or treatment of bacterial infection.

The pharmaceutical composition may be a dry powder or a liquid composition having physiological compatibility. The compositions include, in addition to triazolo(4,5-d) pyrimidine derivative, auxiliary substances, preservatives, solvents and/or viscosity modulating agents. By solvent, one means for example water, saline or any other physiological solution, ethanol, glycerol, oil such as vegetable oil or a mixture thereof. By viscosity modulating agent on means for example carboxymethylcellulose.

The Triazolo(4,5-d)pyrimidine derivative of the present invention exhibits its effects through oral, intravenous, intravascular, intramuscular, parenteral, or topical administration, and can be additionally used into a composition for parenteral administration, particularly an injection composition or in a composition for topical administration. It can also be loaded in nanoparticles for nanomedicine applications. It can be used in an aerosol composition. Such aerosol composition is for example a solution, a suspension, a micronised powder mixture and the like. The composition is administered by using a nebulizer, a metered dose inhaler or a dry powder inhaler or any device designed for such an administration.

Examples of galenic compositions include tablets, capsules, powders, pills, syrups, chewing, granules, and the like. These may be produced through well known technique and with use of typical additives such as excipients, lubricants, and binders.

Suitable auxiliary substances and pharmaceutical compositions are described in Remington's Pharmaceutical Sciences, 16th ed., 1980, Mack Publishing Co., edited by Oslo et al. Typically, an appropriate amount of a pharmaceutically-acceptable salt is used in the composition to render the composition isotonic. Examples of pharmaceutically acceptable substances include saline, Ringer's solution and dextrose solution. pH of the solution is preferably from about 5 to about 8, and more preferably from about 7 to about 7.5.

A still further preferred object of the invention is a method of treatment or prevention of bacterial infection in a host mammal in need of such treatment which comprises administering to the host an effective amount of triazolo(4,5-d) pyrimidine derivatives as defined in formula (I),
preferably (1R-(1α, 2α, 3β(1R*, 2*),5β))-3-(7-((2-(3,4-difluorophenyl)cyclopropyl)amino)-5-((3,3,3-trifluoropropyl)thio)3H-1,2,3-triazolo(4,5d)pyrimidin-3-yl)5(hydroxy)cyclopentane-1,2-diol;
(1S-(1α, 2α, 3β(1R*, 2*),5β))-3-(7-((2-(3,4-difluorophenyl)cyclopropyl)amino)-5-(propylthio)(3H-1,2,3-triazolo(4,5d)pyrimidin-3-yl)5(2-hydroxyethoxy)cyclopentane-1,2-diol;
(1S,2S,3R,5S)-3-[7-[(1R,2S)-2-(3,4-difluorophenyl)cyclopropylamino]-5-(propylthio)-3H-[1,2,3]-triazolo[4,5-d]pyrimidin-3-yl]-5-(2-hydroxyethoxy)-1,2-cyclopentanediol);
most preferably (1S,2S,3R,5S)-3-[7-[(1R,2S)-2-(4-fluorophenyl)cyclopropylamino]-5-(propylthio)-3H-[1,2,3]-triazolo[4,5-d]pyrimidin-3-yl]-5-(2-hydroxyethoxy)-1,2-cyclopentanediol) as defined in formula II;
or most preferably (1S,2R,3S,4R)-4-[7-[[(1R,2S)-2-(3,4-Difluorophenyl)cyclopropyl]amino]-5-(propylthio)-3H-1,2,3-triazolo[4,5-d]pyrimidin-3-yl]-1,2,3-cyclopentanetriol, as defined in formula III;
or a pharmaceutical acceptable salt or solvate thereof, or a solvate thereof or a solvate of such a salt.

In another aspect, the invention provides the use of Triazolo(4,5-d)pyrimidine derivatives, preferably (1R-(1α, 2α, 3β(1R*, 2*),5β))-3-(7-((2-(3,4-difluorophenyl)cyclopropyl)amino)-5-((3,3,3-trifluoropropyl)thio)3H-1,2,3-triazolo(4,5-d)pyrimidin-3-yl)5(hydroxy)cyclopentane-1,2-diol;
(1S-(1α, 2α, 3β(1R*, 2*),5β))-3-(7-((2-(3,4-difluorophenyl)cyclopropyl)amino)-5-(propylthio)(3H-1,2,3-triazolo(4,5d)pyrimidin-3-yl)5(2-hydroxyethoxy)cyclopentane-1,2-diol;
(1S,2S,3R,5S)-3-[7-[(1R,2S)-2-(3,4-difluorophenyl)cyclopropylamino]-5-(propylthio)-3H-[1,2,3]-triazolo[4,5-d]pyrimidin-3-yl]-5-(2-hydroxyethoxy)-1,2-cyclopentanediol);
(1S,2S,3R,5S)-3-[7-[(1R,2S)-2-(4-fluorophenyl)cyclopropylamino]-5-(propylthio)-3H-[1,2,3]-triazolo[4,5-d]pyrimidin-3-yl]-5-(2-hydroxyethoxy)-1,2-cyclopentanediol);
and pharmaceutical acceptable salt or solvate thereof, or a solvate thereof or a solvate of such a salt;
and most preferably (1S,2S,3R,5S)-3-[7-[(1R,2S)-2-(3,4-difluorophenyl)cyclopropylamino]-5-(propylthio)-3H-[1,2,3]-triazolo[4,5-d]pyrimidin-3-yl]-5-(2-hydroxyethoxy)-1,2-cyclopentanediol) or a pharmaceutical acceptable salt or solvate thereof, or a solvate thereof or a solvate of such a salt;
as inhibitor of biofilm on a surface, particularly a surface of a biomaterial or of a medical device.

The most preferred inhibitor of biofilm on a surface is (1S,2R,3S,4R)-4-[7-[[(1R,2S)-2-(3,4-Difluorophenyl)cyclopropyl]amino]-5-(propylthio)-3H-1,2,3-triazolo[4,5-d]pyrimidin-3-yl]-1,2,3-cyclopentanetriol, as defined in formula III

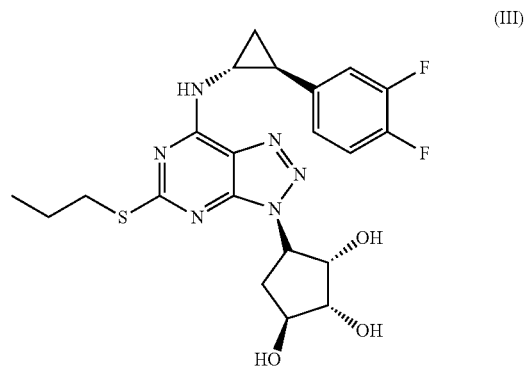

(III)

and pharmaceutical acceptable salt or solvate thereof, or a solvate thereof or a solvate of such a salt;

By surface one means any type of surface such as rubber or plastic surface as for example surface made of polyethylene, polypropylene, polyurethane, polyvinyl chloride, polyvinylpyrrolidone, polytetrafluoroethylene, silicone or the like, or copolymers but also and preferably metallic surface such as stainless steel, silver, gold, titanium, metallic alloys pyrolitic carbon, and the like. It can also be used on bioabsorbable or biomaterial surface such as biological prosthesis or devices which are made of biological material such as for example porcine or bovine pericardium By inhibition of biofilm on a surface one means inhibition of the biofilm formation at all stages of its formation starting from a prevention or an inhibition of adherence of bacteria on the surface at step 1 but also and mainly an inhibition in bacteria grow, multiplication, and formation of microcolonies on the surface at step 2. By inhibition of biofilm one also means inhibition of the matrix at the maturation step 3 and inhibition of bacteria dispersion from the matrix in a colonisation step. By inhibition of biofilm, one also means killing bacteria at all steps of the biofilm formation.

By medical device one means biomaterial as defined above but also medical device requesting no bacterial contamination such as wound dressing, soft tissue fillers, root canal fillers, contact lens, blood bag and the like.

A last further aspect according to the invention, is a method for killing or controlling bacterial growth in biofilm formation on a surface comprising applying Triazolo(4,5-d) pyrimidine derivative on a surface either at a prevention step, reducing bacteria adherence and survival on the substrate or at a stage where the biofilm is already present, or even at a maturation step with a matrix formation wherein a more complex architecture of biofilm is established protecting bacteria as a barrier to conventional antibacterial agent.

The method of bacteria killing or prevention of bacterial growth on a surface is generally applied to biomaterials or medical devices.

The biomaterial or medical device are preferably implantable foreign material for clinical use in host mammals such as prosthetic devices, pacemakers, implantable cardioverter-defibrillators, intravascular catheters, coronary stent, heart valves, intraocular lens and the like but could be extended to other medical devices requesting no bacterial contamination such as for example wound dressings, soft tissue fillers containing local anaesthetics, root canal fillers with ancillary medicinal substances and the like.

The method of bacteria killing or prevention of bacterial growth could also be applied to surface of experimental device in need of such antibacterial treatment.

(A) illustrates a killing curve for methilcillin-resistant *S. aureus* (MRSA).

(B) illustrates a killing curve for Glycopeptide intermediate-resistant *S. aureus* (GISA).

(C) illustrates a killing curve for vancomycin resistant *E. faecalis* (VRE).

Figure 9:
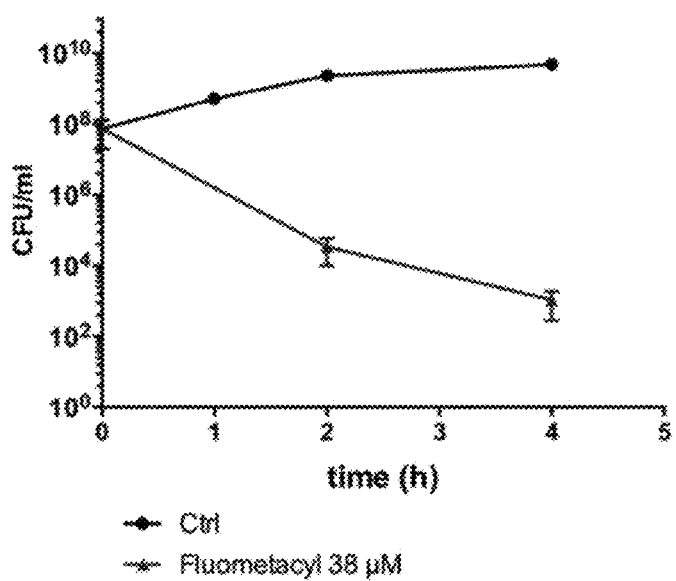

FIG. 9 illustrates bactericidal activity of Fluometacyl against *S. aureus* MRSA.

Figure 10:
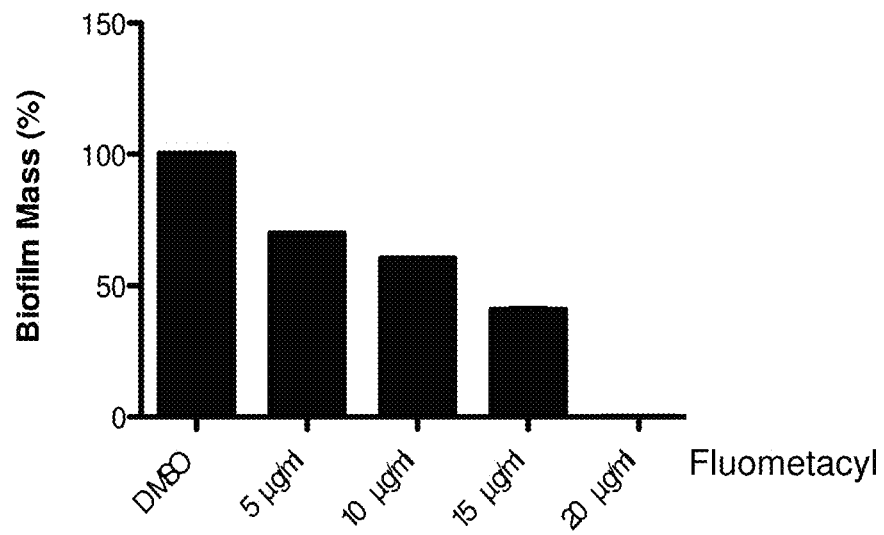
Figure 10:
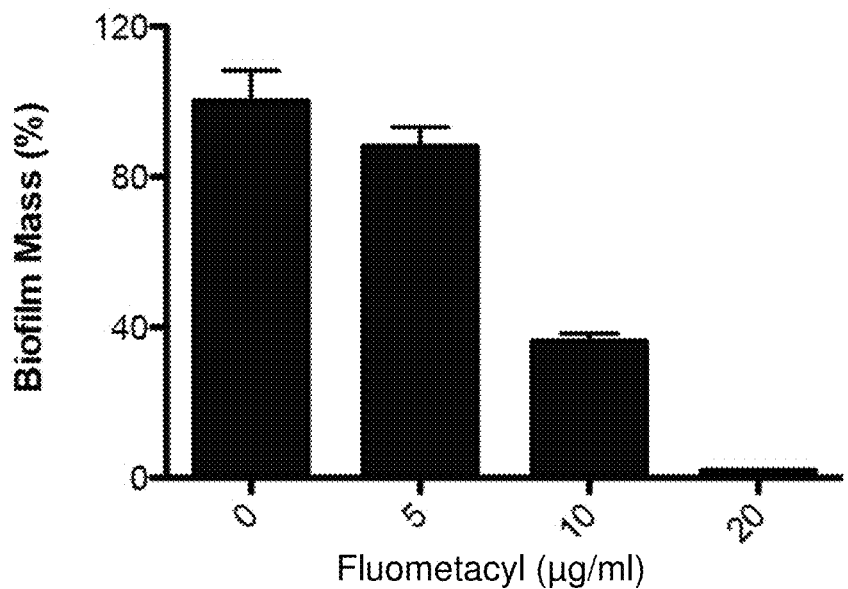

FIGS. 10 (A) and (B) illustrate the antibacterial effect of different concentrations of Fluometacyl on *S. aureus* and *S. epidermidis* biofilm formation respectively.

Figure 11:
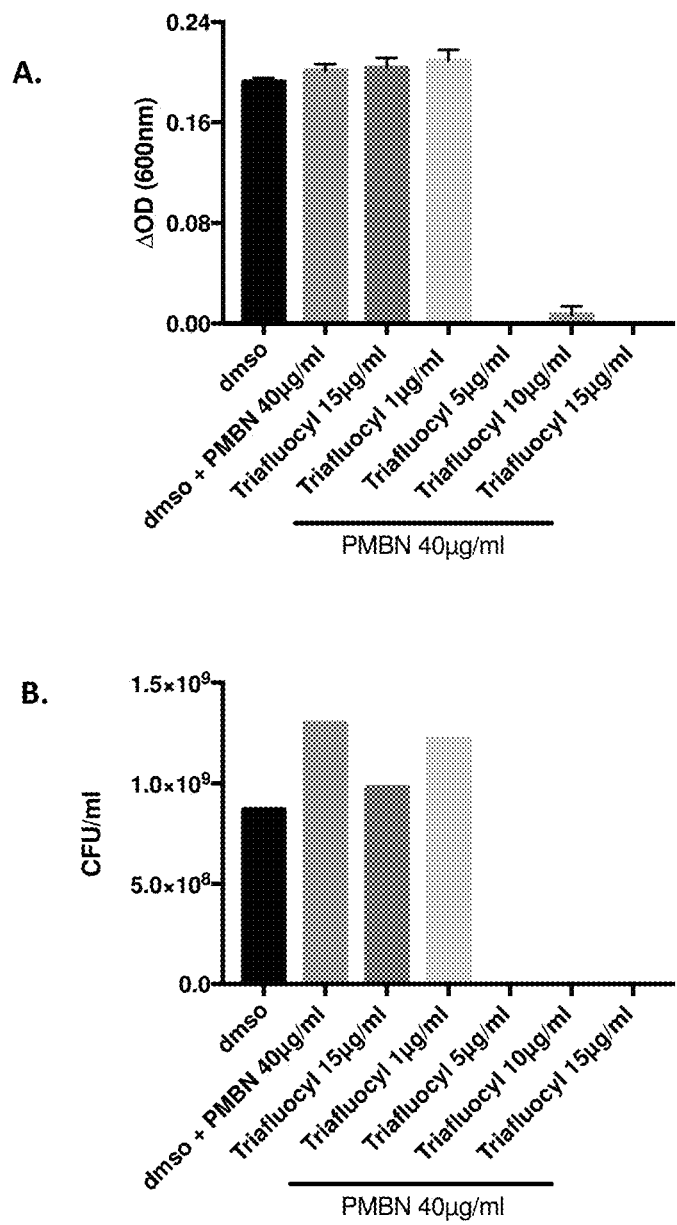

FIG. 11 illustrates an Antibacterial effect of Triafluocyl together with Polymyxin B nonapeptide on *Escherichia coli* (ATCC 8739). Effect of Triafluocyl and polymixin B nonapeptide on the growth of *E. coli* (ATCC 8739) determined by measuring the optical density (A) for MIC determination or the CFU (B) for minimal bactericidal concentration (MBC) after 24 hr incubation at 37° C.

Figure 12:
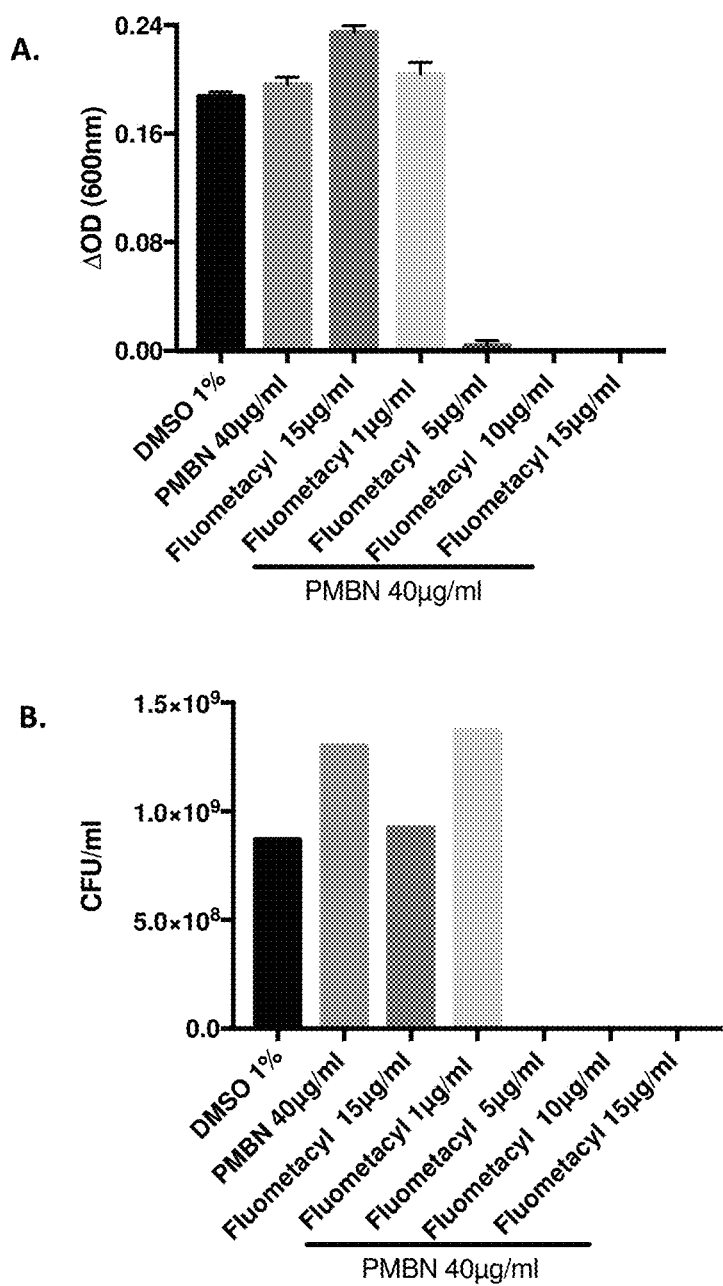

FIG. 12 illustrates an Antibacterial effect of Fluometacyl together with Polymyxin B nonapeptide on *Escherichia coli* (ATCC 8739).

Effect of Fluometacyl and polymixin B nonapeptide on the growth of *E. coli* (ATCC 8739) determined by measuring the optical density (A) for MIC determination or the CFU (B) for minimal bactericidal concentration (MBC) after 24 hr incubation at 37° C.

Figure 13:
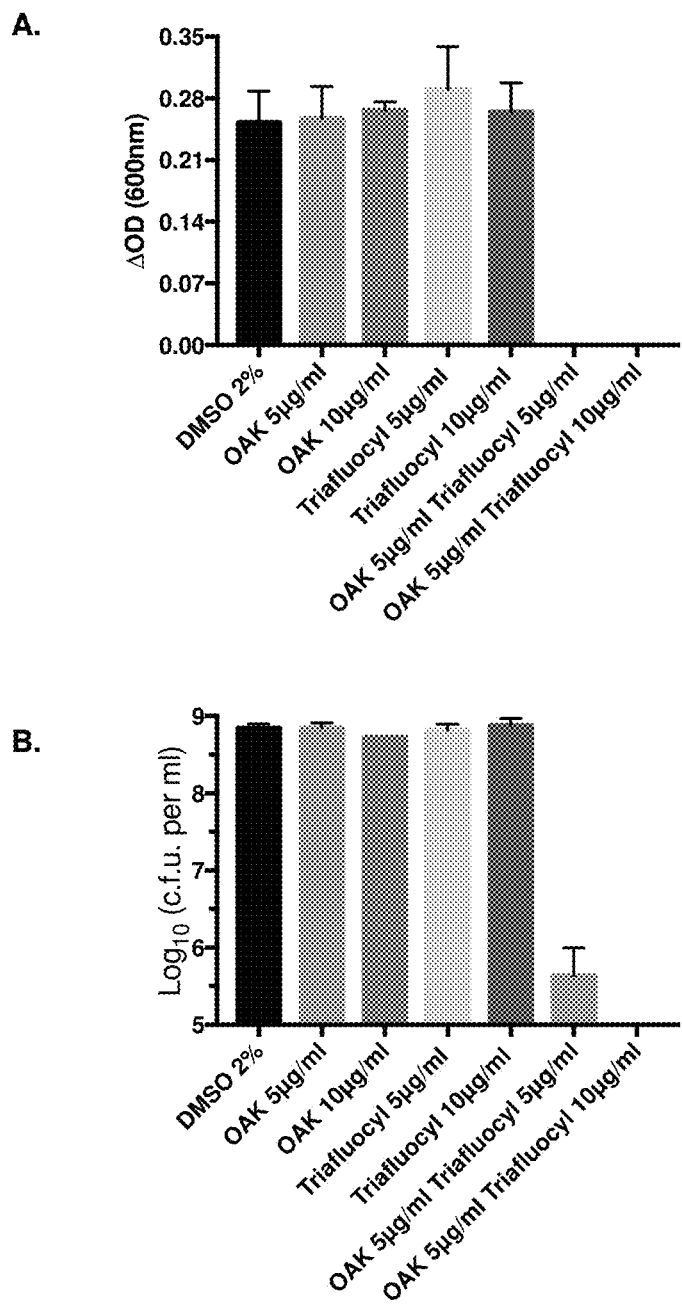

FIG. 13 illustrates an Antibacterial effect of Triafluocyl together with C12($\omega$7)K$\beta$12 on *Escherichia coli* (ATCC 8739). Effect of Triafluocyl and C12($\omega$7)K$\beta$12 on the growth of *E. coli* (ATCC 8739) is determined by measuring the optical density (A) for MIC determination or the CFU (B) for minimal bactericidal concentration (MBC) after 24 hr incubation at 37° C.

Figure 14:
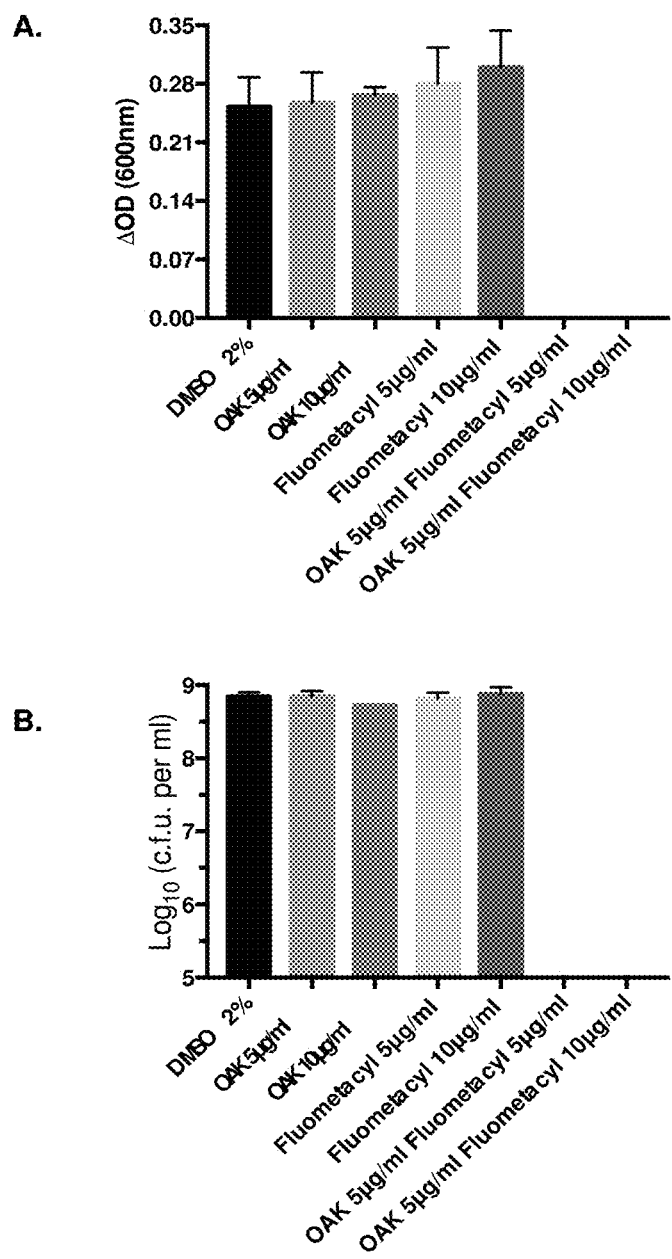

FIG. 14 illustrates an Antibacterial effect of Fluometacyl together with $C_{12(\omega7)}K\beta_{12}$ on *Escherichia coli* (ATCC 8739). Effect of Fluometacyl and $C_{12(\omega7)}K\beta_{12}$ on the growth of *E. coli* (ATCC 8739) is determined by measuring the optical density (A) for MIC determination or the CFU (B) for minimal bactericidal concentration (MBC) after 24 hr incubation at 37° C.

Figure 15:
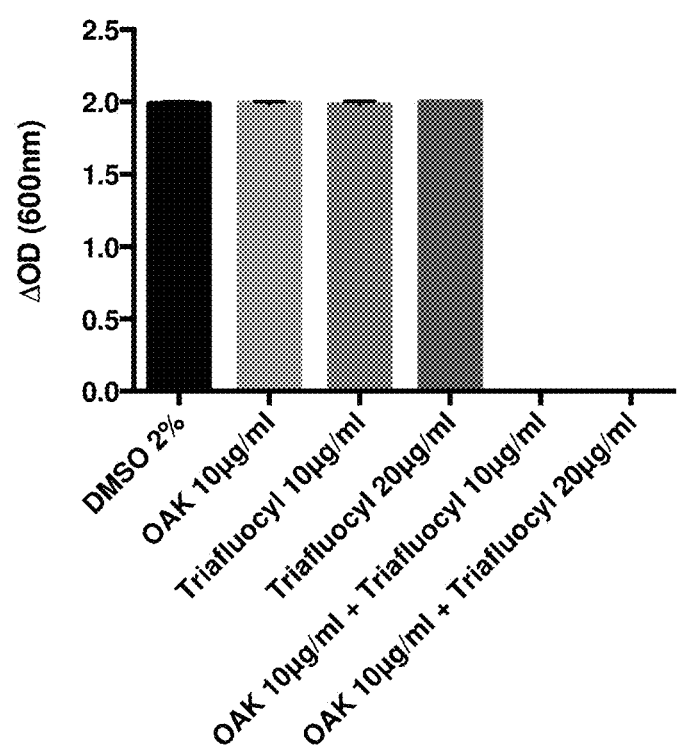

FIG. 15 illustrates an Antibacterial effect of Triafluocyl together with $C_{12(\omega7)}K\beta_{12}$ on *Pseudomonas aeruginosa* (ATCC 27853). Effect of Triafluocyl and $C_{12(\omega7)}K\beta_{12}$ on the growth of *Pseudomonas aeruginosa* is determined by measuring the optical density for MIC determination.

Figure 16:
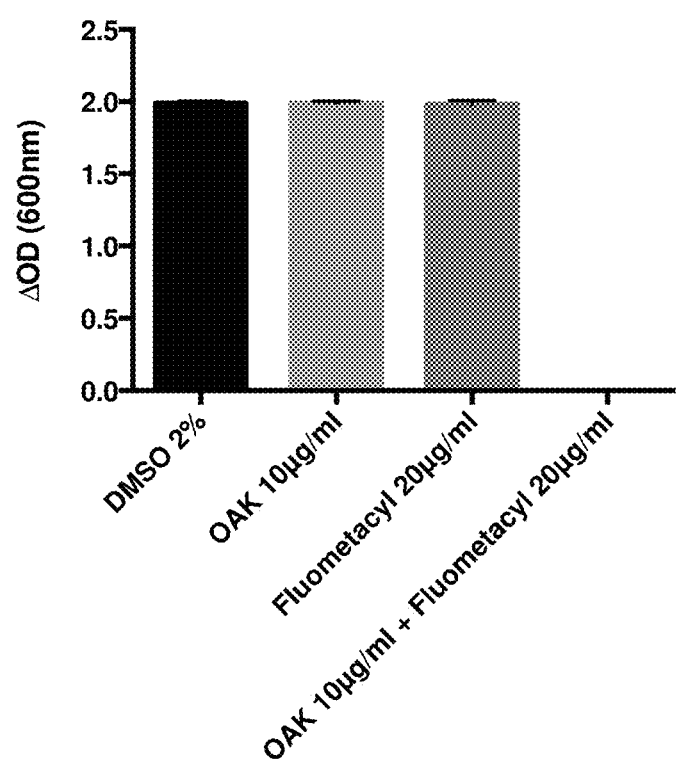

FIG. 16 illustrates an Antibacterial effect of Fluometacyl together with $C_{12(\omega7)}K\beta_{12}$ on *Pseudomonas aeruginosa* (ATCC 27853).

Effect of Fluometacyl and $C_{12(\omega7)}K\beta_{12}$ on the growth of *Pseudomonas aeruginosa* (ATCC 27853) is determined by measuring the optical density for MIC determination.

DESCRIPTION

Examples

The invention is illustrated hereafter by the following non limiting examples.

We have conducted in vitro experiments, using *S. aureus, S. epidermidis*, and *E. faecalis* as clinically relevant Gram-positive bacterial strains.

We have also conducted in vitro experiments, using *Escherichia coli* and *Pseudomonas aeruginosa* as clinically relevant Gram-negative bacterial strains.

The tests were performed in accordance with the recommendations of the European Committee on Antimicrobial Susceptibility Testing (EUCAST).

Fluometacyl (1S,2R,3S,4R)-4-(7-(((1R,2S)-2-(3,4-Difluorophenyl)cyclopropyl)amino)-5-((propyl)thio)-3H-[1,2,3]triazolo[4,5-d]pyrimidin-3-yl)cyclopentane-1,2,3-triol may be synthesized according to the process described in WO 99/05143.

Example 1

Use of (1S,2S,3R,5S)-3-[7-[(1R,2S)-2-(3,4-difluorophenyl)cyclopropylamino]-5-(propylthio)-3H-[1,2,3]-triazolo[4,5-d]pyrimidin-3-yl]-5-(2-hydroxyethoxy)-1,2-cyclopentanediol) or Triafluocyl (Cayman, item No 15425)

*S. aureus* (American Type Culture Collection, ATCC 25904) was grown overnight in Tryptic Soy Broth (TSB) medium, diluted 1:100 in fresh TSB, and incubated aerobically at 37° C. until bacteria growth reached a logarithmic phase ($OD_{600}$=0.25-0.3).

Increasing concentrations of Triafluocyl (Cayman Chemical, Item No. 15425) or vehicle (DMSO) was then added in 5 ml of bacteria suspensions. Bacterial growth was measured after different time intervals (20-100 min) by spectrophotometry ($OD_{600}$) and by counting the colony-forming units after plating appropriate culture dilutions on TS agar plates.

Figure 1:
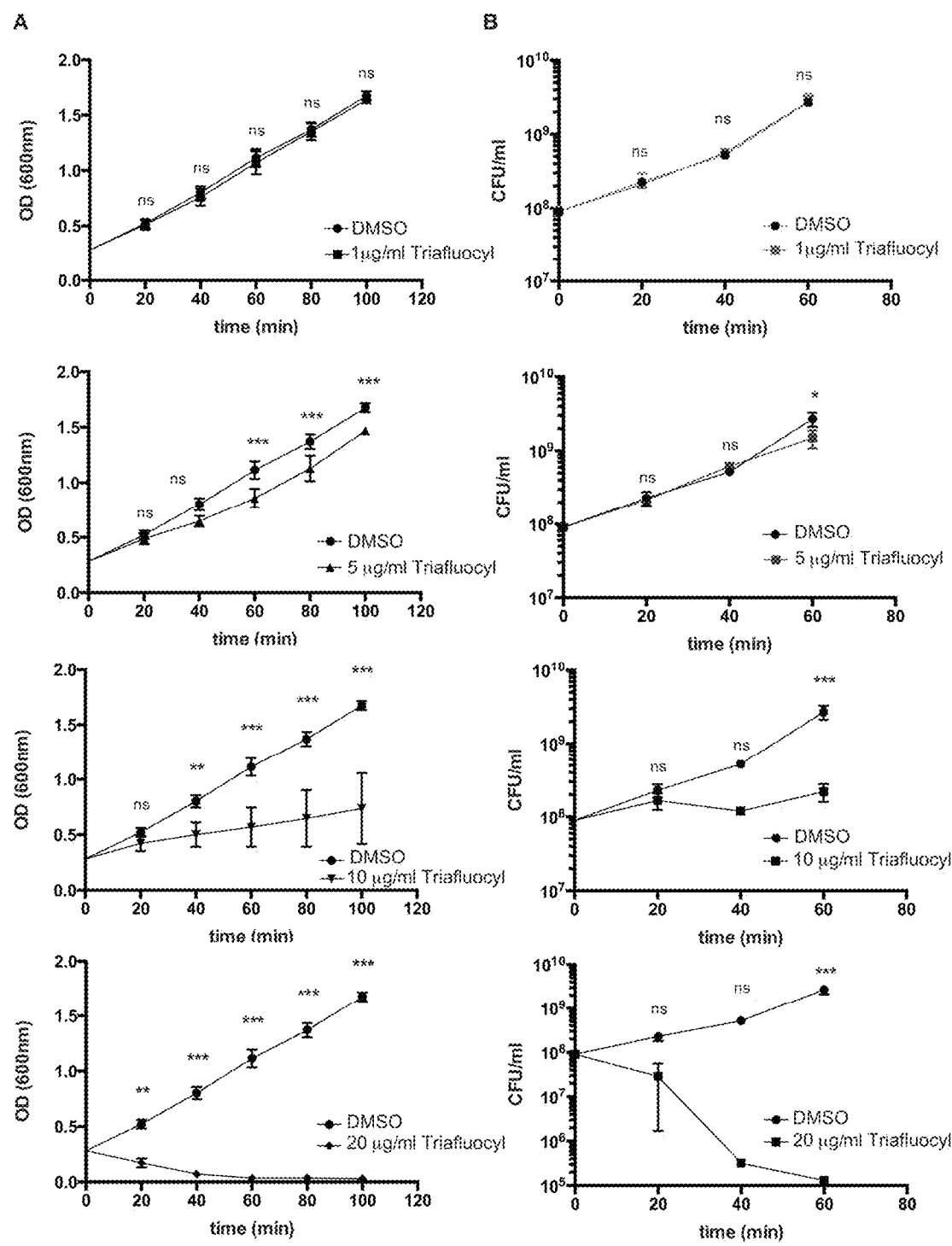
FIG. 1 illustrates a bacteriostatic and bactericidal effect of Triafluocyl on *Staphylococcus aureus*. Growth curves (A) and viable counts (B) in the presence of different concentrations of Triafluocyl or DMSO as vehicle are shown.

Bacteriostatic and bactericidal effects were measured with Triafluocyl. In FIG. 1 kinetics of S. aureus growth in the presence of an increasing concentrations (1 μg/ml to 20 μg/ml) of Triafluocyl were measured by turbidity measurement (upper graph), and viable count (lower graph). Data represent medians±range (n=3). *p<0.05; p<0.01; *p<0.001, Triafluocyl vs vehicle.

As shown in FIG. 1, while a concentration of 10 μg/ml Triafluocyl was able to inhibit bacterial growth, 20 μg/ml Triafluocyl displayed potent bactericidal effect.

Example 2

Use of (1S,2S,3R,5S)-3-[7-[(1R,2S)-2-(3,4-difluorophenyl) cyclopropylamino]-5-(propylthio)-3H-[1,2,3]-triazolo[4,5-d]pyrimidin-3-yl]-5-(2-hydroxyethoxy)-1,2-cyclopentanediol) or Triafluocyl as Inhibitor of Biofilm Formation S. aureus (ATCC 25904) was grown overnight in TSB medium, before being diluted 100 fold in fresh TSB, and incubated aerobically at 37° C. until bacteria culture reached an $OD_{600}$ of 0.6 (corresponding to approximately $1-3 \times 10^8$ CFU/ml). Bacteria cultures were then diluted to $1 \times 10^4$ CFU/ml in fresh TSB. 800 μl aliquots of diluted bacteria suspensions were distributed in each well of a 24-well plate. Bacteria were allowed to adhere for 4 hours under static conditions at 37° C. After removing media, wells were rinsed 2 times with PBS to eliminate planktonic bacteria and re-filled with TSB supplemented with 0.5% glucose Triafluocyl or DMSO as vehicle was then added at desired concentration and plates were incubated at 37° C. for 20 hours. After incubation, wells were washed and stained with 0.5% (w/v) crystal violet for 30 minutes, washed again and the dye was solubilized by adding 20% acetic acid (v/v in water) before reading absorbance at 595 nm.

Figure 2:
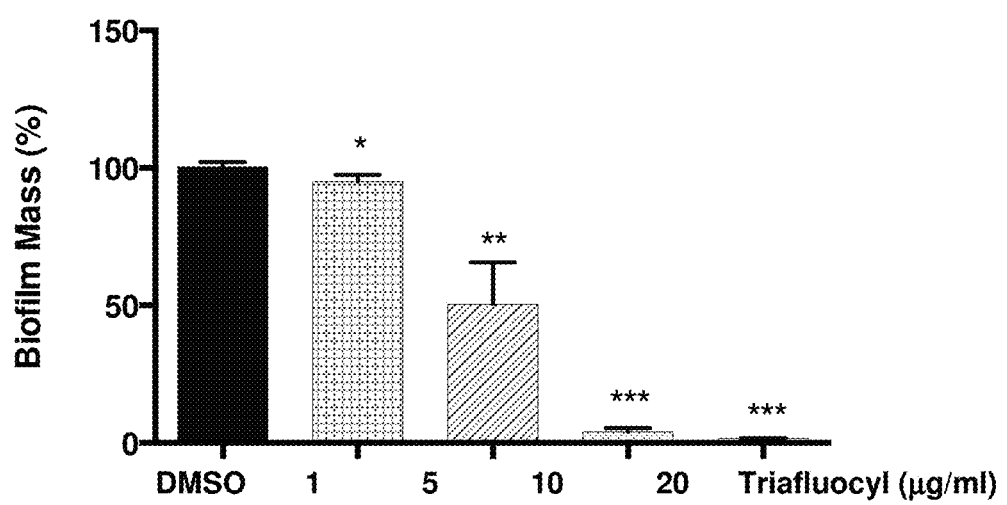
FIG. 2 illustrates an inhibition of *Staphylococcus aureus* biofilm formation by Triafluocyl at stage 2.

S. aureus biofilms were formed on polystyrene surface in the presence of increasing concentrations of Triafluocyl or DMSO as vehicle. In FIG. 2, Biofilm mass is presented as percentage of values obtained in the presence of DMSO (*P<0.05; P<0.01; *P<0.001, Triafluocyl versus DMSO, n=4).

Triafluocyl significantly reduces S. aureus biofilm formation at all concentrations tested. In the presence of 10 μg/ml Triafluocyl, no biofilm could form on polystyrene surface.

Example 3

Use of (1S,2S,3R,5S)-3-[7-[(1R,2S)-2-(3,4-difluorophenyl)cyclopropylamino]-5-(propylthio)-3H-[1,2,3]-triazolo[4,5-d]pyrimidin-3-yl]-5-(2-hydroxyethoxy)-1,2-cyclopentanediol) or Triafluocyl (Cayman Chemical, Item No. 15425)

E. faecalis (ATCC 29212) was grown overnight in Brain heart infusion (BHI) medium, diluted 1:100 in fresh BHI, and incubated aerobically at 37° C. until bacteria growth reached a logarithmic phase ($OD_{600}$=0.25-0.3).

Increasing concentrations of Triafluocyl (Cayman Chemical, Item No. 15425) or DMSO as vehicle was then added in 5 ml of bacteria suspensions. Bacterial growth was measured after different time intervals (30-120 min) by spectrophotometry ($OD_{600}$) and by counting the colony-forming units after plating appropriate culture dilutions on BHI agar plates.

Figure 3:
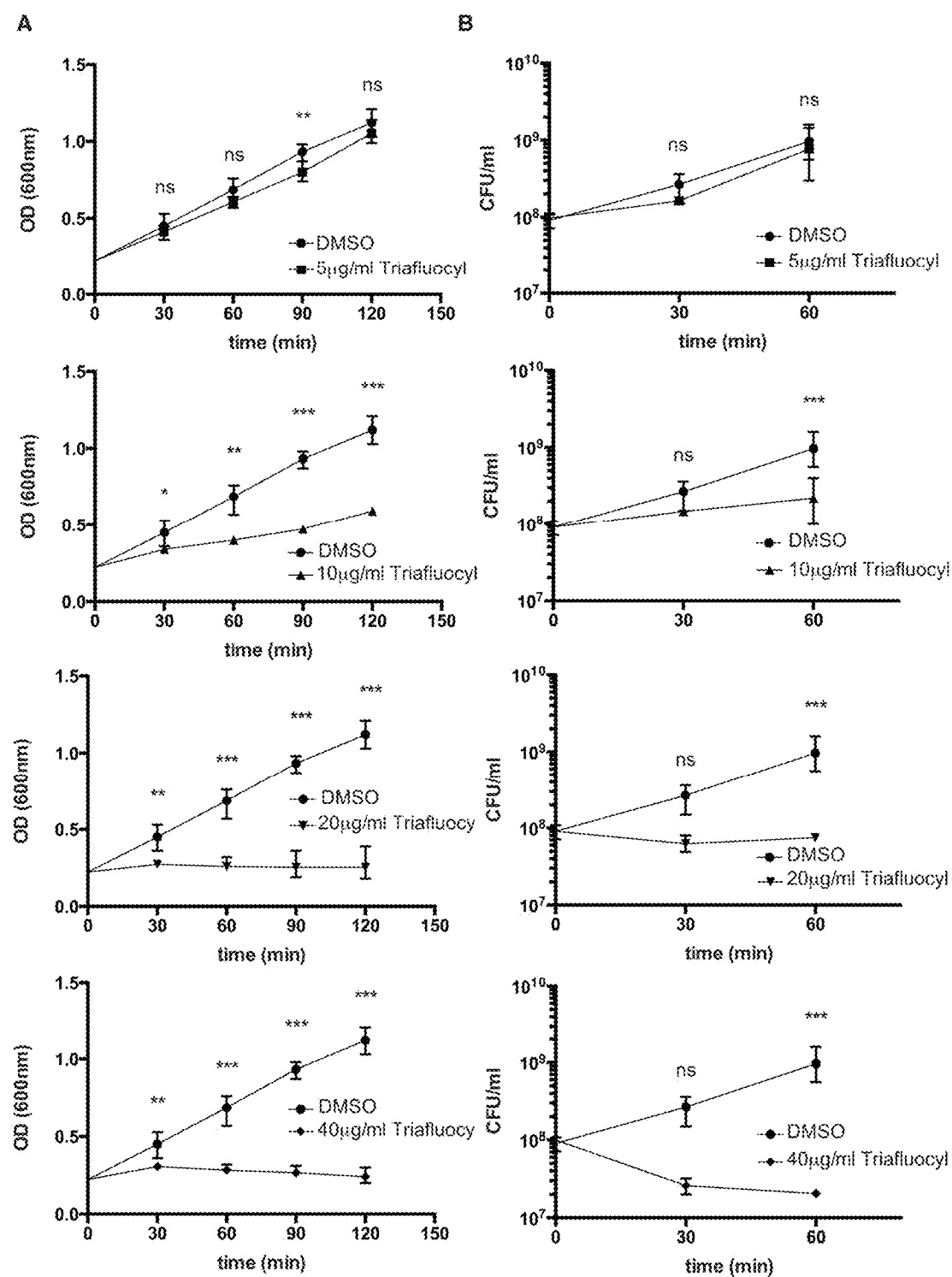
FIG. 3 illustrates a bacteriostatic and bactericidal effect of Triafluocyl on *Enterococcus faecalis*. Growth curves (A) and viable count (B) in the presence of different concentrations of Triafluocyl or DMSO as vehicle are shown.
Figure 4:
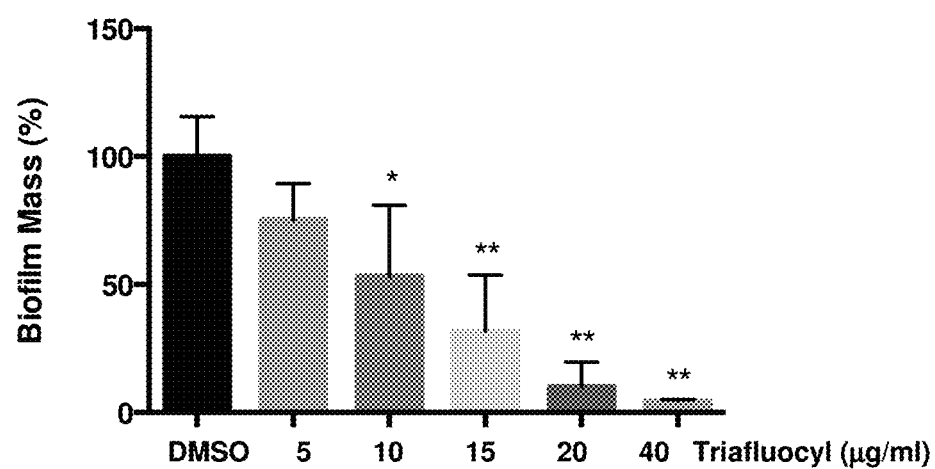
FIG. 4 illustrates an inhibition of *Enterococcus faecalis* biofilm formation by Triafluocyl at stage 2.

Bacteriostatic and bactericidal effects were measured with Triafluocyl. In FIG. 3 kinetics of E. faecalis growth in the presence of an increasing concentrations (5 μg/ml to 40 μg/ml) of Triafluocyl were measured by turbidity measurement (upper graph), and viable count (lower graph). Data represent medians±range (n=3).

As shown in FIG. 3, while a concentration of 10 μg/ml Triafluocyl was able to inhibit bacterial growth, 20 μg/ml Triafluocyl and more importantly 40 μg/ml displayed potent bactericidal effects.

Example 4

Use of Triafluocyl as Inhibitor of Biofilm Formation

E. faecalis (ATCC 29212) was grown overnight in BHI medium, before being diluted 100 fold in fresh TSB, and incubated aerobically at 37° C. until bacteria culture reached an $OD_{600}$ of 0.6 (corresponding to approximately $2-5 \times 10^8$ CFU/ml). Bacteria cultures were then diluted to $1 \times 10^4$ CFU/ml in fresh TSB. 800 μl aliquots of diluted bacteria suspensions were distributed in each well of a 24-well plate. Bacteria were allowed to adhere for 4 hours under static conditions at 37° C. After removing media, wells were rinsed 2 times with PBS to eliminate planktonic bacteria and re-filled with TSB supplemented with 0.5% glucose Triafluocyl or DMSO as vehicle was then added at desired concentration and plates were incubated at 37° C. for 20 hours. After incubation, wells were washed and stained with 0.5% (w/v) crystal violet for 30 minutes, washed again and the dye was solubilized by adding 20% acetic acid (v/v in water) before reading absorbance at 595 nm.

E. faecalis biofilms were formed on polystyrene surface in the presence of increasing concentrations of Triafluocyl or DMSO as vehicle. In FIG. 2, Biofilm mass is presented as percentage of values obtained in the presence of DMSO (*P<0.05; P<0.01; *P<0.001, Triafluocyl versus DMSO, n=4).

Triafluocyl significantly reduces E. faecalis biofilm formation at a starting concentration of 10 μg/ml. In the presence of 40 μg/ml Triafluocyl, no biofilm could form on polystyrene surface.

Example 5

Time-Kill Study of Triafluocyl Against S. epidermidis

To evaluate Triafluocyl antibacterial effect we have tested S. epidermidis liquid growth in the presence of different Triafluocyl concentrations in logarithmic phase. In this phase usually bacteria are highly susceptible to agents with bactericidal activity because they are rapidly dividing.

A 1:100 inoculum in 50 ml TSB of an O/N culture of S. epidermidis was cultured for 3 hr up to its logarithmic phase ($OD_{600}$=0.26 and ≈$3 \times 10^8$ CFU/ml).

Bacteria were split in several tubes containing different concentrations of DMSO as vehicle alone or in combination with Triafluocyl in TSB and grown for 100 min at 37° C. with 220 rpm shaking, the $OD_{600}$ was measured every 20 min.

Figure 5:
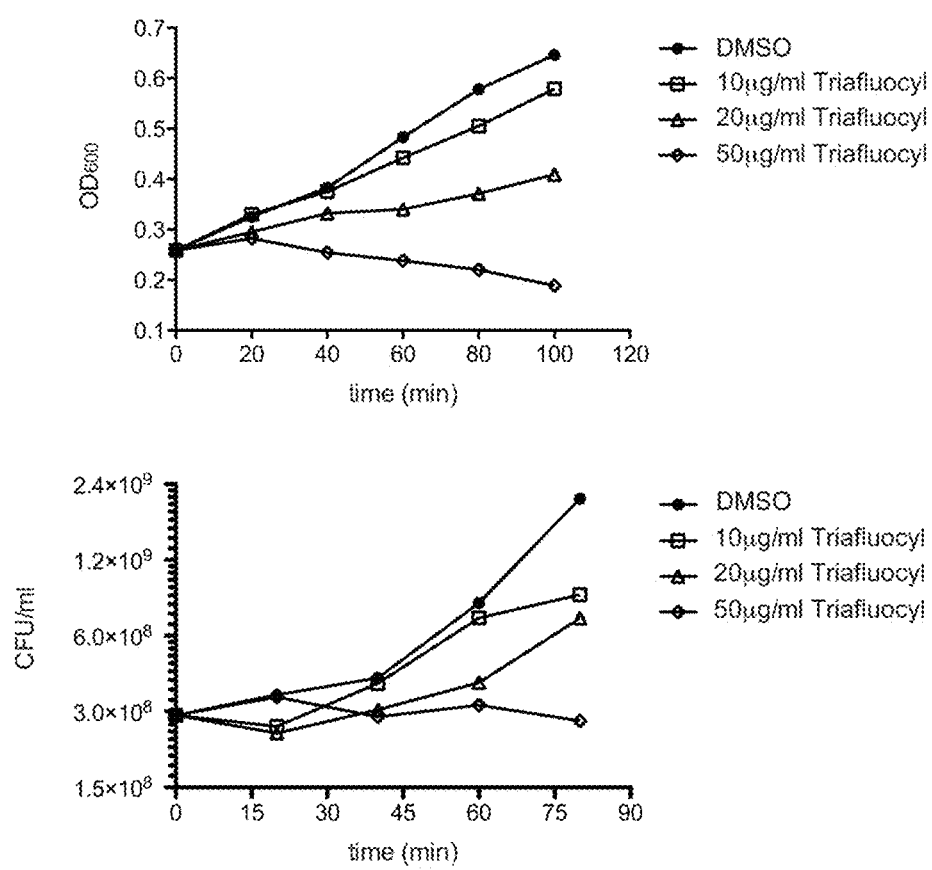
FIG. 5 illustrates a bacteriostatic and bactericidal effect of Triafluocyl on *Staphylococcus epidermidis*. Growth curve (upper panel) and viable count (lower panel) in the presence of different concentrations of Triafluocyl or DMSO as vehicle.

Compared to the growth with DMSO (0.25%) we observed a dose-dependent inhibition of S. epidermidis growth between 10 µg/ml and 20 µg/ml Triafluocyl (FIG. 5). At 50 µg/ml we observed a slight bacteriostatic activity, confirmed by the number of viable cells at 80 min, $3 \times 10^8$ CFU/ml, equal to the number of bacteria in the untreated control at the beginning of the assay (FIG. 5).

Moreover, we have tested the effect of Triafluocyl on a low-density inoculum, $0.08 \times 10^6$ CFU/ml, from a culture of *S. epidermidis* in logarithmic phase. We have followed the growth for 4 hr with or without Triafluocyl and measured the $OD_{600}$: already 5 µg/ml of Triafluocyl decreased the OD by 50% compared to the growth in absence of Triafluocyl at the same time point; 10 µg/ml and 20 µg/ml inhibited growth (OD value equal to OD at the beginning of the growth) (data not shown).

This means that the lower the inoculum density the lower the concentration of Triafluocyl to slow down growth or kill bacteria.

Example 6

Triafluocyl Prevents *S. epidermidis* Biofilm Formation

To study the effect of Triafluocyl on biofilm formation, *S. epidermidis* in early logarithmic phase ($5 \times 10^8$ CFU/ml) was plated in a 24-well plate and let to adhere at the bottom of the well for 4 hr at 37° C. in static conditions. After 4 hr incubation, planktonic bacteria were removed and adherent bacteria were washed twice in TSB. Fresh TSB medium supplemented or not with 0.25% glucose was added to the well with 5 different concentrations of Triafluocyl and incubated for 24 hours. Wells were washed 3 times with NaCl 0.9% and incubated for 1 hr at RT with Crystal Violet 1% solution in $dH_2O$ to stain the biofilm.

Wells were washed 3 times with $dH_2O$ to eliminate unbound crystal violet, then 400 µl Acetic Acid 10% was added and incubated at RT for 10 min. Absorbance was measured in triplicate at 570 nm, reflecting total biomass of the biofilm (live and dead bacteria).

Figure 6:
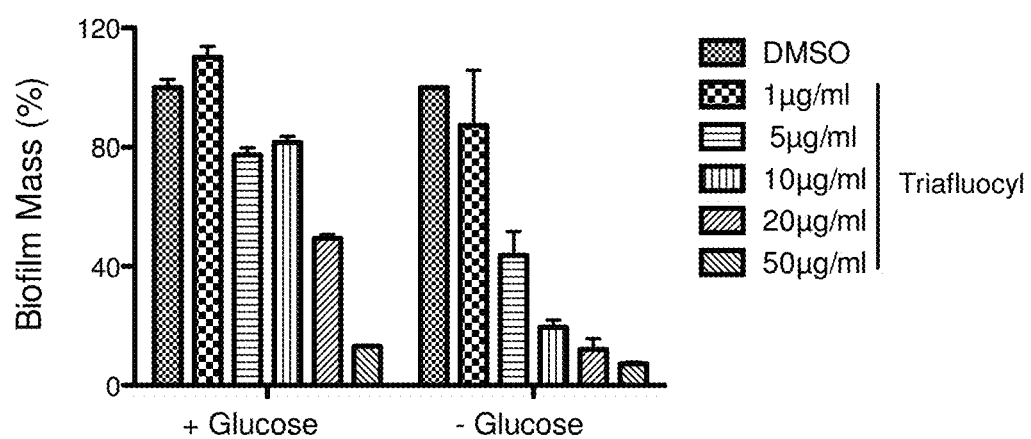
FIG. 6 illustrates an inhibition of *Staphylococcus epidermidis* biofilm formation at stage 2 by Triafluocyl.

Triafluocyl affected biofilm formation (FIG. 6): already at 5 µg/ml, in the absence of glucose, it inhibited biofilm formation by 50%, while in presence of glucose we reach 50% biofilm reduction only at 20 µg/ml Triafluocyl.

The concentration of Triafluocyl that inhibits at least 90% biofilm formation is called minimum biofilm inhibitory concentration (MBIC). Triafluocyl MBIC for *S. epidermidis* is 50 µg/ml both in the presence and in the absence of glucose.

Example 7

Triafluocyl Destroys *S. epidermidis* Mature Biofilm

In another experiment we let adhere $0.5 \times 10^8$ CFU/ml *S. epidermidis* cells for 4 hr and let the biofilm form for additional 24 hr in presence of 0.25% glucose, at this point we treated the biofilm with several concentrations of Triafluocyl for 24 hr in TSB with 0.25% glucose and determined the viable count (FIG. 7) as well as the percentage of live cells using the BacLight bacterial viability kit (Molecular Probes).

For biofilm analysis, we first washed the biofilm to eliminate all planktonic bacteria and then the biofilm was detached mechanically using a scraper. To assure that the aggregates from the biofilm were completely dissociated, the suspension of cells was passed through a needle (0.5×16 mm) and a dilution was plated on TSA plates.

Only the highest concentration of Triafluocyl, 50 µg/ml, was effective in reducing the number of viable cells in the biofilm with a reduction of almost 3 log (from $1.1 \times 10^8$ CFU/ml in the control to $1.5 \times 10^5$ CFU/ml).

Figure 7:
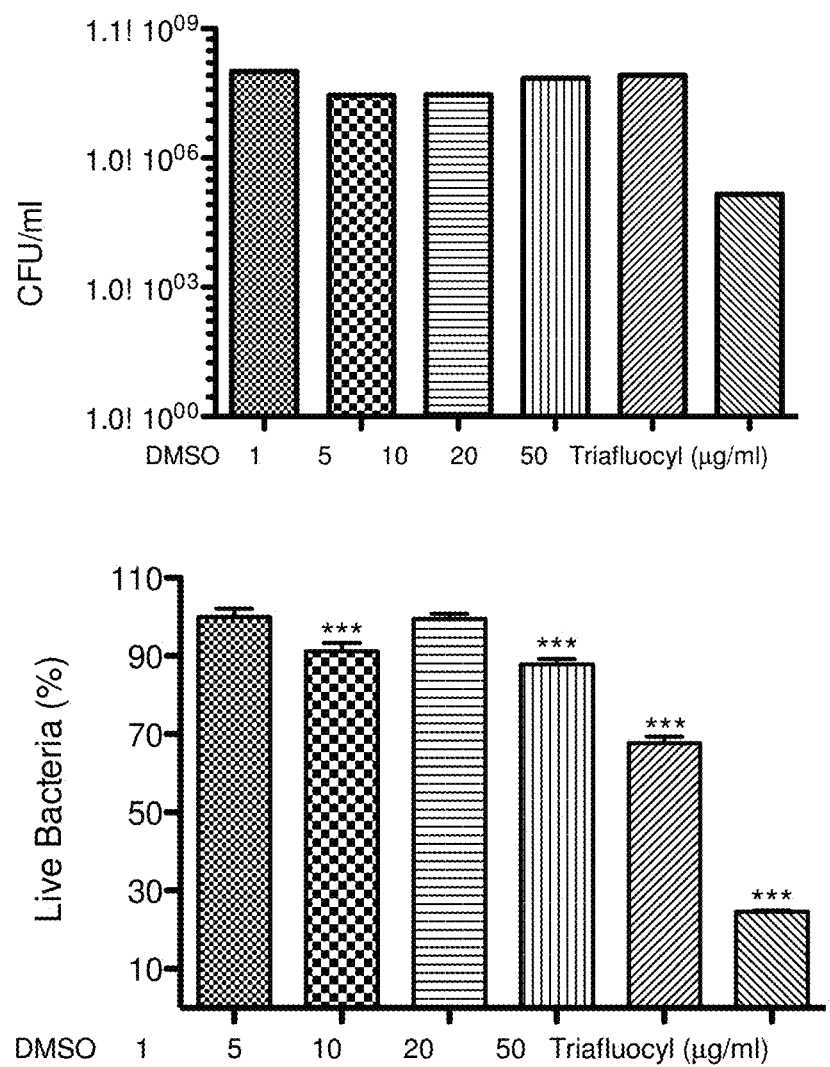
FIG. 7 illustrates a destruction of mature biofilm (stage 3: 24-hour biofilm) by Triafluocyl. Viable count of *S. epidermidis* biofilm after a 24h treatment with Triafluocyl (upper panel). Percentage of live cells in the biofilm (lower panel).

In the same experiment we also determined the percentage of live and dead bacteria. To do so we followed the procedure of the kit LIVE/DEAD from Molecular Probes. Briefly, the biofilm was resuspended in a solution of 0.9% NaCl and cells were stained with a mixture of SYTO9 (green fluorescence) and propidium iodide (PI) (red fluorescence) for 15 min in the dark. Stained cells were transferred in a 96-well plate and fluorescence was measured using the Enspire Spectrophotometer with excitation wavelength of 470 nm and emission spectra in the range of 490-700 nm. SYTO9 dye (green fluorescence 500-520 nm) penetrates all the cells (dead and live) and binds to DNA, while PI (red fluorescence in the range 610-630 nm) enters only in dead cells with a damaged cell membrane. When PI and SYTO9 are in the same cell the green fluorescence intensity decreases. Therefore, in a population of cells with high percentage of dead cells there is a reduction in the emission spectra of the green fluorescence, because there is more PI staining. The ratio of fluorescence intensity (green/live) is plotted against a known percentage of live cells to obtain a standard curve and the percentage of live cells in our samples is obtained by extrapolation (FIG. 7). Triafluocyl, at concentrations of 20 µg/ml and 50 µg/ml reduced the percentage of live bacteria to 80% and 30%, respectively.

Example 8

Triafluocyl Antibacterial Effects on *S. epidermidis*: Determination of Minimal Inhibitory Concentration (MIC) and Minimal Bactericidal Concentration (MBC)

The Minimal Inhibitory Concentration (MIC) and the Minimal Bactericidal Concentration (MBC) of Triafluocyl were determined in *Staphylococcus epidermidis* (ATCC 35984, also known as RP62A) according to EUCAST (European Committee on Antimicrobial Susceptibility Testing) recommendations.

Briefly, a single colony grown on a Tryptic Soy Agar (TSA) plate was resuspended and cultured in Tryptic Soy Broth (TSB) overnight (O/N) in aerobic conditions (37° C. with 220 rpm shaking), next day a 1:50 inoculum in Mueller-Hinton broth (MHB) was incubated in aerobic conditions for 3 hr and an inoculum of 1:100 dilution, corresponding to $3 \times 10^5$ CFU/ml, was incubated in presence or absence of different concentrations of Triafluocyl in 1% DMSO (vehicle). After O/N growth the OD of each culture was measured at 600 nm in a spectrophotometer ($OD_{600}$). The MIC represents the concentration at which there is no visible growth of bacteria, i.e. $\Delta OD$ at 600 nm equal to zero (blank is the medium alone).

We have also determined the MBC, i.e. the concentration at which the liquid culture, when spread on TSA plates, will not produce any colony.

The MIC for Triafluocyl against *S. epidermidis* is equal to $12 \pm 3$ µg/ml and the MBC is $17 \pm 3$ µg/ml (two biological replicates, detection limit $10^{-3}$).

The Minimum Duration for killing 99.9% *S. epidermidis* (MDK99.9) by Triafluocyl, a tolerance metric according to the EUCAST, was 2 hours.

Example 9

Triafluocyl Antibacterial Effects on S. aureus: Determination of Minimal Inhibitory Concentration (MIC) and Minimal Bactericidal Concentration (MBC)

Further experiments were conducted using different strains of S. aureus, as clinically relevant Gram-positive bacterial strains: ATCC 25904, ATCC 6538, methilcillin-resistant S. aureus (MRSA) ATCC BAA-1556, Glycopeptide intermediate-resistant (GISA) S. aureus Mu-50 (ATCC 700695) in order to determine the Minimal Inhibitory Concentration (MIC) which is the minimal concentration required to prevent bacterial growth; the Minimal Bactericidal Concentration (MBC) which determines the lowest concentration at which an antimicrobial agent kill a particular microorganism and a Minimum Duration for killing 99.9% bacteria (MDK99.9) which is a tolerance metric according to the EUCAST.

MIC determination: A single colony selected from the different strains of S. aureus is resuspended and cultured in the appropriate medium overnight (O/N) in aerobic conditions (37° C. with 220 rpm shaking), next day a 1:100 inoculum in Mueller-Hinton broth (MHB) was incubated in aerobic conditions for 3 hr (OD=0.08-0.1) and an inoculum of 1:300 dilution, corresponding to $3 \times 10^5$ CFU/ml, was incubated in presence or absence of different concentrations of Triafluocyl in 1% DMSO. After O/N growth the OD of each culture was measured at 600 nm in a spectrophotometer ($OD_{600}$). The MIC represents the concentration at which there is no visible growth of bacteria, i.e. ΔOD at 600 nm equal to zero (blank is the medium alone). MIC for Triafluocyl against S. aureus ATCC 25904, ATCC 6538, methilcillin-resistant S. aureus (MRSA) ATCC BAA-1556, Glycopeptide intermediate-resistant (GISA), and S. aureus Mu-50 (ATCC 700695) were 20, 20, 15, and 20 µg/ml, respectively.

MBC and MDK99.9 determination: A single colony selected from the different strains of S. aureus is resuspended and cultured in the appropriate medium (TSB, or BHI) overnight (O/N) in aerobic conditions (37° C. with 220 rpm shaking), next day a 1:100 inoculum in the appropriate medium was incubated in aerobic conditions for 2 h. The culture is then challenged with triafluocyl at MIC concentration or higher concentrations. Bacterial growth was measured after different time intervals by counting the colony-forming units after plating appropriate culture dilutions on BHI agar plates. The concentration that kill at least 99.9% of the started inoculum in 24 h is defined as the MBC. And the real time needed is defined as the $MDK_{99.9}$. MBC for Triafluocyl against S. aureus ATCC 25904, ATCC 6538, methilcillin-resistant S. aureus (MRSA) ATCC BAA-1556, Glycopeptide intermediate-resistant (GISA), and S. aureus Mu-50 (ATCC 700695) were 20 µg/ml for each of them. $MDK_{99.9}$ for Triafluocyl against S. aureus ATCC 25904, ATCC 6538, methilcillin-resistant S. aureus (MRSA) ATCC BAA-1556, Glycopeptide intermediate-resistant (GISA), and S. aureus Mu-50 (ATCC 700695) were 10, 6, 2, and 14 hours, respectively.

Example 10

Triafluocyl Antibacterial Effects on E. faecalis: Determination of Minimal Inhibitory Concentration (MIC) and Minimal Bactericidal Concentration (MBC)

Further experiments were conducted using different strains of E. faecalis, as clinically relevant Gram-positive bacterial strains: E. faecalis vancomycin-resistant (VRE) ATCC BAA-2365, and E. faecalis ATCC 29212 in order to determine the Minimal Inhibitory Concentration (MIC) which is the minimal concentration required to prevent bacterial growth; the Minimal Bactericidal Concentration (MBC) which determines the lowest concentration at which an antimicrobial agent kill a particular microorganism and a Minimum Duration for killing 99.9% bacteria (MDK99.9) which is a tolerance metric according to the EUCAST.

MIC determination: A single colony selected from the different strains of E. faecalis is resuspended and cultured in the appropriate medium overnight (O/N) in aerobic conditions (37° C. with 220 rpm shaking), next day a 1:100 inoculum in Mueller-Hinton broth (MHB) was incubated in aerobic conditions for 3 hr (OD=0.08-0.1) and an inoculum of 1:300 dilution, corresponding to $3 \times 10^5$ CFU/ml, was incubated in presence or absence of different concentrations of Triafluocyl in 1% DMSO. After O/N growth the OD of each culture was measured at 600 nm in a spectrophotometer ($OD_{600}$). The MIC represents the concentration at which there is no visible growth of bacteria, i.e. ΔOD at 600 nm equal to zero (blank is the medium alone). MIC for Triafluocyl against E. faecalis vancomycin-resistant (VRE) ATCC BAA-2365, and E. faecalis ATCC 29212 were 20 and 40 µg/ml, respectively.

MBC and MDK99.9 determination: A single colony selected from the different strains of E. faecalis is resuspended and cultured in the appropriate medium (TSB, or BHI) overnight (O/N) in aerobic conditions (37° C. with 220 rpm shaking), next day a 1:100 inoculum in the appropriate medium was incubated in aerobic conditions for 2 h. The culture is then challenged with triafluocyl at MIC concentration or higher concentrations. Bacterial growth was measured after different time intervals by counting the colony-forming units after plating appropriate culture dilutions on BHI agar plates. The concentration that kill at least 99.9% of the started inoculum in 24h is defined as the MBC. And the real time needed is defined as the $MDK_{99.9}$. MBC for Triafluocyl against E. faecalis vancomycin-resistant (VRE) ATCC BAA-2365 was 20 µg/ml. $MDK_{99.9}$ for Triafluocyl against E. faecalis vancomycin-resistant (VRE) ATCC BAA-2365 was 24 hours.

Example 11

Triafluocyl Antibacterial Effects on Streptococcus agalactiae: Determination of Minimal Inhibitory Concentration (MIC) and Minimal Bactericidal Concentration (MBC)

Further experiments were conducted using S. agalactiae (ATCC 12386), as clinically relevant Gram-positive bacterial strains in order to determine the Minimal Inhibitory Concentration (MIC) which is the minimal concentration required to prevent bacterial growth; the Minimal Bactericidal Concentration (MBC) which determines the lowest concentration at which an antimicrobial agent kill a particular microorganism and a Minimum Duration for killing 99.9% bacteria (MDK99.9) which is a tolerance metric according to the EUCAST.

MIC determination: A single colony selected from the different strains of S. agalactiae (ATCC 12386) is resuspended and cultured in the appropriate medium overnight (O/N) in aerobic conditions (37° C. with 220 rpm shaking), next day a 1:100 inoculum in Mueller-Hinton broth (MHB) was incubated in aerobic conditions for 3 hr (OD=0.08-0.1) and an inoculum of 1:300 dilution, corresponding to $3 \times 10^5$ CFU/ml, was incubated in presence or absence of different concentrations of Triafluocyl in 1% DMSO. After O/N growth the OD of each culture was measured at 600 nm in a spectrophotometer ($OD_{600}$). The MIC represents the concentration at which there is no visible growth of bacteria, i.e. ΔOD at 600 nm equal to zero (blank is the medium alone). MIC for Triafluocyl against *S. agalactiae* (ATCC 12386) was 40 µg/ml.

MBC and MDK99.9 determination: A single colony selected from *S. agalactiae* (ATCC 12386) is resuspended and cultured in the appropriate medium (TSB, or BHI) overnight (O/N) in aerobic conditions (37° C. with 220 rpm shaking), next day a 1:100 inoculum in the appropriate medium was incubated in aerobic conditions for 2 h. The culture is then challenged with triafluocyl at MIC concentration or higher concentrations. Bacterial growth was measured after different time intervals by counting the colony-forming units after plating appropriate culture dilutions on BHI agar plates. The concentration that kill at least 99.9% of the started inoculum in 24 h is defined as the MBC. And the real time needed is defined as the $MDK_{99.9}$. MBC for Triafluocyl against *S. agalactiae* (ATCC 12386) was 40 µg/ml. $MDK_{99.9}$ for Triafluocyl against *S. agalactiae* (ATCC 12386) was 1 hour.

Figure 8:
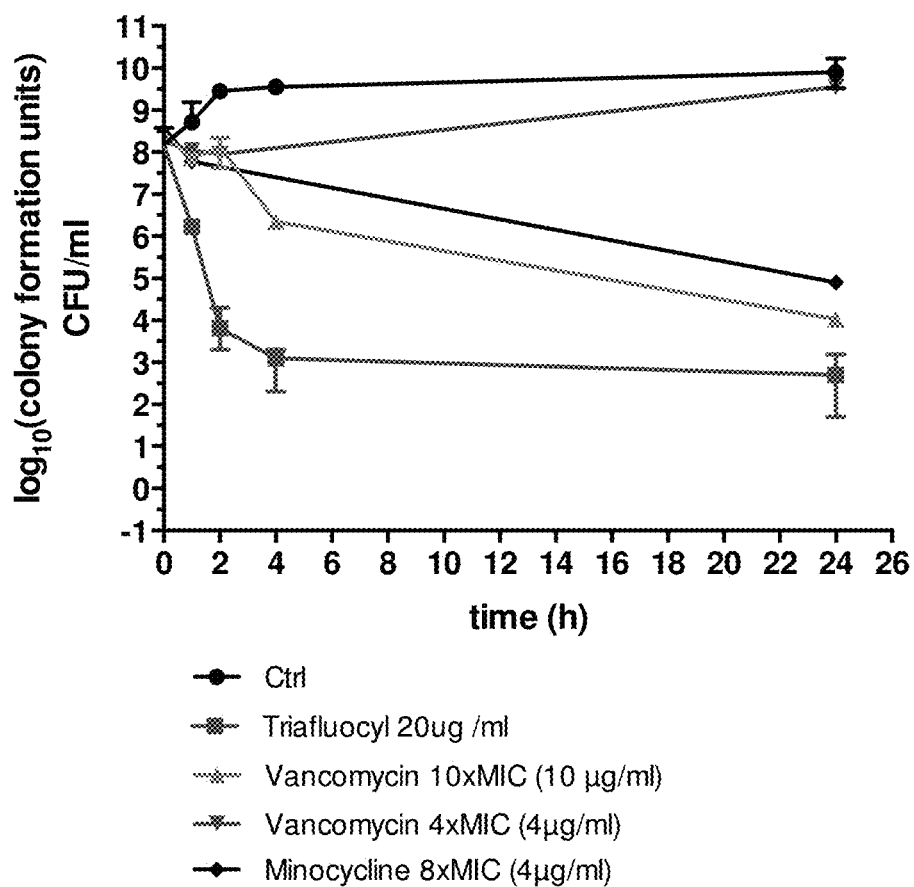
FIG. 8 illustrates bactericidal activity against MRSA, GISA and VRE strains of Triafluocyl as compared to Vancomycin and Mynocycline.
Figure 8:
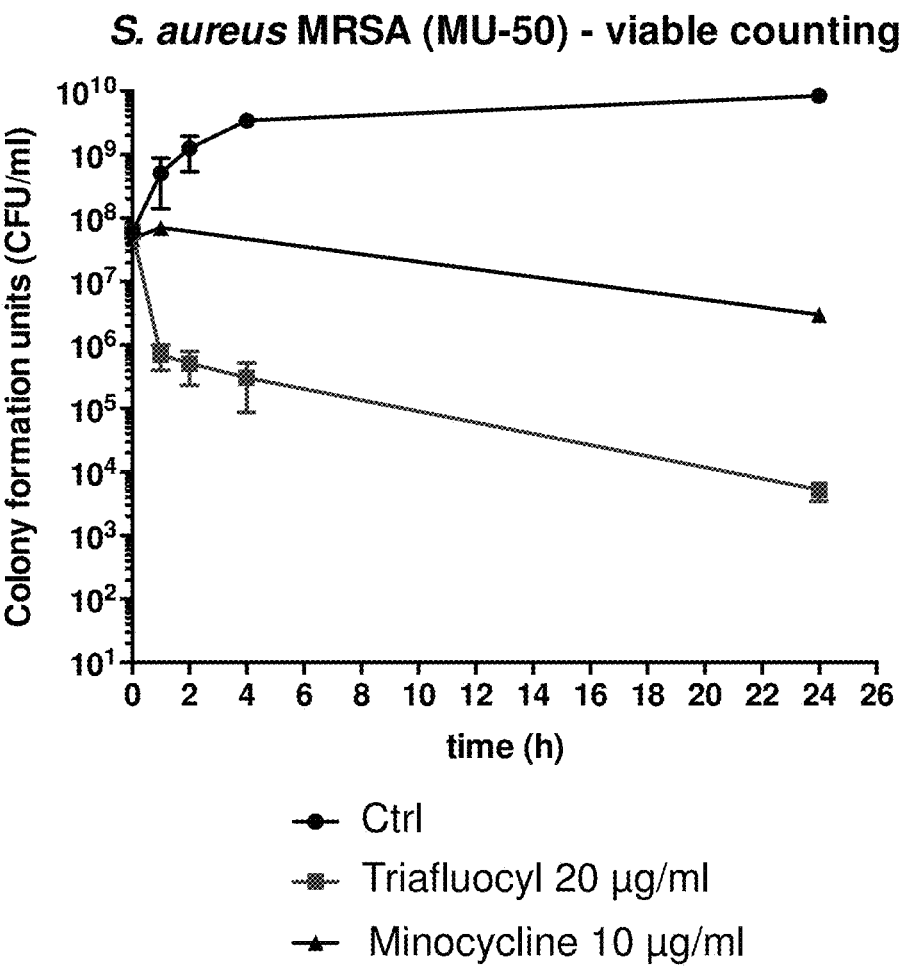
Figure 8:
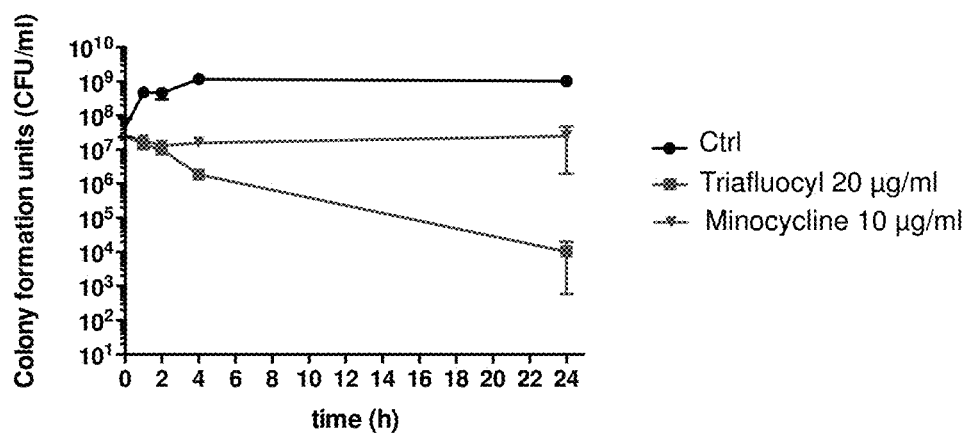

The results of all experiments are illustrated in Table 1 and in FIGS. 8 A,B,C, wherein the effect of Triafluocyl on resistant strains such as MRSA: methilcillin-resistant *S. aureus*; GISA: Glycopeptide intermediate-resistant *S. aureus*; VRE: vancomycin-resistant *E. faecalis* is shown.

TABLE 1

MIC: minimal inhibitory concentration; MBC: minimal bactericidal concentration (cut-off = 99.9% reduction in CFU); MDK99.9: time(h) needed to kill 99.9% of the started inoculum; nd: not determined.

| Strains | Resistance | MIC µg/ml | MBC µg/ml | MDK 99.9 Time (h) |
|---|---|---|---|---|
| *S. aureus* (ATCC25904) | | 20 | 20 | 10 |
| *S. aureus* (ATCC6538) | | 20 | 20 | 6 |
| *S. aureus* | MRSA | 15 | 20 | 2 |
| *S. aureus*-Mu50 | GISA | 20 | 20 | 14 |
| *S. epidermidis* | | 15 | 20 | 2 |
| *E. faecalis* | | 40 | nd | nd |
| *E. faecalis* | VRE | 20 | 20 | 24 |
| *S. agalactiae* | | 40 | 40 | 1 |

FIG. 8A also illustrates a comparison between the antibacterial effects of Triafluocyl, Vancomycin and Minocycline on MRSA.

*S. aureus* MRSA (ATCC BAA-1556) was grown overnight in brain heart infusion (BHI) medium, diluted 1:100 in fresh BHI, and incubated aerobically at 37° C. until bacteria growth reached a logarithmic phase ($OD_{600}$=0.25-0.3).

Triafluocyl (Cayman Chemical, Item No. 15425) (20 µg/ml), Vancomycin (Sigma, 4 µg/ml or 10 µg/ml), Minocycline (Sigma, 8 µg/ml) or a solvent (DMSO) were added to 5 ml of *S. aureus* MRSA suspensions.

Bacterial growth for *S. aureus* MRSA was measured after different time intervals by counting the colony-forming units after plating appropriate culture dilutions on BHI agar plates.

One clearly observes that Triafluocyl causes a decrease of *S. aureus* MRSA viable count as early as after the first two hours, at which time doses of Vancomycin and Minocycline equal to 10- and 8-fold MIC, respectively, were ineffective. Over the 24 h-experiment, the bactericidal effect of Vancomycin and Minocyclin remained less efficient than the one of Triafluocyl.

FIG. 8B) illustrates a comparison between the antibacterial effect of Triafluocyl and Minocycline on *S. aureus* GISA.

*S. aureus* Mu50 GISA was grown overnight in brain heart infusion (BHI) medium, diluted 1:100 in fresh BHI, and incubated aerobically at 37° C. until bacteria growth reached a logarithmic phase ($OD_{600}$=0.25-0.3).

Triafluocyl (Cayman Chemical, Item No. 15425) (20 µg/ml), Minocycline (Sigma, 8 µg/ml) or vehicle (DMSO) were then added in 5 ml of bacteria suspensions. Bacterial growth was measured after different time intervals by counting the colony-forming units after plating appropriate culture dilutions on BHI agar plates.

Here again Triafluocyl (20 µg/ml) had a quicker and more efficient antibacterial effect than a high dose of Minocycline (10 µg/ml).

FIG. 8C illustrates a comparison between Triafluocyl and Minocycline on *E. faecalis* VRE.

*E. faecalis* VRE (ATCC BAA-2365) was grown overnight in brain heart infusion (BHI) medium, diluted 1:100 in fresh BHI, and incubated aerobically at 37° C. until bacteria growth reached a logarithmic phase ($OD_{600}$=0.2-0.25).

Triafluocyl (Cayman Chemical, Item No. 15425) (20 µg/ml), Minocycline (Sigma, 10 µg/ml) or vehicle (DMSO) was then added in 5 ml of bacteria suspensions. Bacterial growth was measured after different time intervals by counting the colony-forming units after plating appropriate culture dilutions on BHI agar plates.

Here Triafluocyl (20 µg/ml) showed bactericidal effect while a high dose of Minocycline (10 µg/ml) was only bacteriostatic.

Example 12

Fluometacyl Antibacterial Effects on Gram-Positive Bacteria Strains: *S. aureus, S. epidermidis, E. faecalis*

Susceptibility Testing: MIC and MBC Determination:

The Minimal Inhibitory Concentration (MIC) and the Minimal Bactericidal Concentration (MBC) of Fluometacyl were determined on several gram-positive strains (Table 2) following EUCAST (European Committee on Antimicrobial susceptibility Testing) recommendations.

For MIC determination a single colony was resuspended and cultured in the appropriate bacteria-specific medium (TSB: Tryptic Soy Broth for *S. aureus* atcc 25904 and *S. epidermidis* and BHI: brain-heart infusion medium for all the other strains) overnight (O/N) in aerobic conditions (37° C. with 220 rpm shaking), next day a 1:100 inoculum was incubated in Mueller-Hinton broth (MHB) in aerobic conditions for 3 hr ($OD_{600}$=0.08-0.1). A further inoculum, 1:300 dilution of the MHB culture, corresponding to $3 \times 10^5$ CFU/ml, was grown in presence or absence of different concentrations of Fluometacyl, 1% DMSO in MHB for 20 hr.

For MBC determination a 1:100 inoculum of an O/N culture (prepared like before) was incubated in aerobic conditions for 2 h in bacteria-specific medium. The culture was then challenged with Fluometacyl at the MIC concentration or higher. Bacterial growth was measured after different time intervals by counting the colony-forming units (CFU) after plating appropriate culture dilutions on bacteria-specific medium agar plates. The concentration that kills at least 99.9% of the started inoculum in 24 h is defined as the MBC.

TABLE 2

MIC and MBC determination for different strains. MRSA: methilcillin-resistant *S. aureus*; GISA: Glycopeptide intermediate-resistant *S. aureus*; VRE: vancomycin-resistant *Enteroccocus*. MIC: minimal inhibitory concentration; MBC: minimal bactericidal concentration (cut-off = 99.9% reduction in CFU).

| Strains | Resistance | MIC µM | MBC µM |
|---|---|---|---|
| *S. aureus* (ATCC25904) |  | 30-38 | 38 |
| *S. aureus* | MRSA | 20-30 | 38 |
| *S. aureus*-MU50 | GISA | 30-38 | 38 |
| *S. epidermidis* |  | 30 | 38 |
| *E. faecalis* | VRE | 38 | 38 |

Time-Kill Study of Fluometacyl against Methilcillin-Resistant *S. aureus*

*S. aureus* MRSA (ATCC BAA-1556) was grown overnight in BHI medium, then a 1:100 inoculum was diluted in fresh BHI and incubated aerobically at 37° C. until bacteria growth reached a logarithmic phase ($OD_{600}$=0.25-0.3). The culture was split into two and challenged with 38 µM Fluometacyl (=18.2 µg/ml) or DMSO (Ctrl). Bacterial growth was measured after different time intervals by counting the colony-forming units after plating appropriate culture dilutions on BHI agar plates. (N=2)

Example 13

Fluometacyl Antibacterial Effects on Biofilm Formation

*Staphyloccocus aureus* (ATCC 25904) or *Staphyloccocus epidermidis* (ATCC 35984) were grown overnight in TSB medium, before being diluted 100 fold in fresh TSB, and incubated aerobically at 37° C. until bacteria culture reached an $OD_{600}$ of 0.6 (corresponding to approximately 1-3×10$^8$ CFU/ml). Bacteria cultures were then diluted to 1×10$^4$ CFU/ml in fresh TSB. Aliquots of 800 µl diluted bacteria suspensions were distributed in each well of a 24-well plate. Bacteria were allowed to adhere for 4 hours under static conditions at 37° C. After removing the media, wells were rinsed 2 times with PBS to eliminate planktonic bacteria and re-filled with TSB supplemented with 0.5% glucose containing Fluometacyl at desired concentration or DMSO alone (Ctrl). The 24-well plates were incubated at 37° C. for 20 hours. Wells were then washed and stained with 0.5% (w/v) crystal violet for 30 minutes and rinsed with PBS 4 times. The dye was solubilized by adding 20% acetic acid (v/v in water) before reading absorbance at 595 nm. FIG. 10A and FIG. 10B show Fluometacyl effect on *S. aureus* and *S. epidermidis* biofilm formation respectively at all concentrations tested. In presence of 38 µM Fluometacyl, both *S. aureus* and *S. epidermidis* could not form any biofilm.

Example 14

Triafluocyl Antibacterial Effects on *Escherichia coli* (ATCC 8739) Together with Polymyxin B Nonapeptide (PMBN) as Membrane Penetrating Agent Determination of Minimal Inhibitory Concentration (MIC) and Minimal Bactericidal Concentration (MBC) of Triafluocyl (Cayman Chemical, Item No. 15425) in presence of polymyxin B nonapeptide (PMBN) (Sigma-Aldrich Merk, Item No. P2076) against *Escherichia coli* (ATCC 8739).

The Minimal Inhibitory Concentration (MIC) represents the concentration, in a liquid culture, at which there is no visible growth of bacteria after 24 h incubation (no pellet or cloudiness), i.e. ΔOD at 600 nm equal to zero wherein ΔOD is the difference between the resulting optical density (OD) with the molecule together with PMBN, and the optical density (OD) of the blank (blank is the medium alone).

The MBC represents the lowest concentration of drug required to kill the bacteria in a liquid culture.

Triafluocyl stock solution of 100 mg/ml is prepared by adding to 50 mg Triafluocyl vial, provided by Cayman Chemical, 500 µl of DMSO (Sigma-Aldrich Merk, Item No. D2650). Following dissolution in DMSO Triafluocyl is further diluted in DMSO to 20 mg/ml working solution. Both the stock and working solution are stored at −20° C.

PMBN stock solution is prepared in water at 10 mg/ml and stored at −20° C.

A single colony grown on a Luria-Bertani Agar (LB) plate was resuspended and cultured in LB medium overnight (O/N) in aerobic conditions (37° C. with 220 rpm shaking), next day a 1:50 inoculum in Mueller-Hinton broth (MHB) is incubated in aerobic conditions for 1 h30 (OD=0.08-0.1) and an inoculum corresponding to 3×10$^6$ colony forming unit (CFU)/ml, is incubated in presence or absence of different concentrations of Triafluocyl in 1% DMSO with or without 40 µg/ml Polymyxin B nonapeptide (PMBN) for 18 hr in aerobic conditions (37° C. with 220 rpm shaking). Growth of *Escherichia coli* in 7 conditions depicted in FIG. 11 is evaluated by reading the OD of each culture at 600 nm ($OD_{600}$) in a spectrophotometer (Victor 3-Perkin Elmer).

The MIC for Triafluocyl in presence of 40 µg/ml PMBN against *Escherichia coli* (ATCC 8739) is equal to 5 µg/ml. Triafluocyl taken alone in concentrations up to 15 µg/ml or PMBN alone up to 40 µg/ml are unable to inhibit *E. coli* growth (FIG. 11A).

The Minimal Bactericidal Concentration (MBC) of Triafluocyl in presence of 40 µg/ml PMBN against *Escherichia coli* (ATCC 8739) is equal to 5 µg/ml (FIG. 11B). To determine the MBC, several dilutions of each culture are spread on LB agar plates to evaluate the number of colony forming unit (CFU) after 24 hr incubation at 37° C.

Example 15

Fluometacyl Antibacterial Effects on *Escherichia coli* (ATCC 8739) Together with Polymyxin B Nonapeptide (PMBN) as Membrane Penetrating Agent Determination of Minimal Inhibitory Concentration (MIC) and Minimal Bactericidal Concentration (MBC) of Fluometacyl in presence of polymyxin B nonapeptide (PMBN) (Sigma-Aldrich Merk, Item No. P2076) against *Escherichia coli* (ATCC 8739).

The Minimal Inhibitory Concentration (MIC) represents the concentration, in a liquid culture, at which there is no visible growth of bacteria (no pellet or cloudiness), i.e. ΔOD at 600 nm equal to zero wherein ΔOD is the difference between the resulting optical density (OD) with the molecule together with PMBN, and the optical density (OD) of the blank (blank is the medium alone).

The MBC represents the lowest concentration of drug required to kill the bacteria in a liquid culture.

Fluometacyl stock solution of 20 mg/ml is prepared by adding 250 µl DMSO (Sigma-Aldrich Merk, Item No. D2650) to 5 mg Fluometacyl powder. The stock is stored at −20° C.

PMBN stock solution is prepared in water at 10 mg/ml and stored at −20° C.

A single colony grown on a Luria-Bertani Agar (LB) plate is resuspended and cultured in LB medium overnight (O/N) in aerobic conditions (37° C. with 220 rpm shaking), next day a 1:50 inoculum in Mueller-Hinton broth (MHB) is incubated in aerobic conditions for 1 h30 (OD=0.08-0.1) and an inoculum corresponding to $3 \times 10^6$ colony forming unit (CFU)/ml is incubated in presence or absence of different concentrations of Fluometacyl in 1% DMSO (vehicle) with or without 40 µg/ml Polymyxin B nonapeptide (PMBN) for 18 hr in aerobic conditions (37° C. with 220 rpm shaking). Growth of bacteria in the 7 individual cultures (FIG. 12A) is evaluated by reading the OD of each culture at 600 nm ($OD_{600}$) in a spectrophotometer (Victor 3-Perkin Elmer).

The MIC for Fluometacyl in presence of 40 µg/ml PMBN against *Escherichia coli* (ATCC 8739) is equal to 5 µg/ml. Fluometacyl taken alone in concentrations up to 15 µg/ml or PMBN alone up to 40 µg/ml is unable to inhibit *E. coli* growth (FIG. 12A).

The Minimal Bactericidal Concentration (MBC) of Fluometacyl in presence of 40 µg/ml PMBN against *Escherichia coli* (ATCC 8739) is equal to 5 µg/ml (FIG. 12B). To determine the MBC, several dilutions of each culture are spread on LB agar plates to evaluate the number of colony forming unit (CFU) after 24 hr incubation at 37° C.

Example 16

Triafluocyl Antibacterial Effects on *Escherichia coli* (ATCC 8739)

(together with a Oligo-Acyl-Lysine (OAK) as membrane penetrating agent: the $C_{12(\omega 7)}K\beta_{12}$, also called cis-7-dodecenoyl-lysyl-lysyl-aminododecanoyl-lysyl-amide).

Determination of Minimal Inhibitory Concentration (MIC) and Minimal Bactericidal Concentration (MBC) of Triafluocyl (purchased from Cayman Chemical, Item No. 15425) in presence of $C_{12(\omega 7)}K\beta_{12}$ (purchased from biomers.net, Germany) against *Escherichia coli* (ATCC 8739). The $C_{12(\omega 7)}K\beta_{12}$ was synthesized by solid-phase method as described by I. Radzishevsky in Antimicrobial Agents and Chemotherapy, May 2007 (1753-1759) (https://aac.asm.org/content/51/5/1753).

The Minimal Inhibitory Concentration (MIC) represents the concentration, in a liquid culture, at which there is no visible growth of bacteria after 24 hours incubation (no pellet or cloudiness), i.e. ΔOD at 600 nm equal to zero, wherein ΔOD is the difference between the resulting optical density (OD) with Triafluocyl together with $C_{12(\omega 7)}K\beta_{12}$, and the optical density (OD) of the blank (blank being the medium alone).

The Minimal Bactericidal Concentration (MBC) represents the lowest concentration of Triafluocyl together with $C_{12(\omega 7)}K\beta_{12}$ required to kill over a period of 24 hours at least 99.9% of bacteria present at time zero in a liquid culture. Viable count in the liquid culture is estimated by counting the colony forming units (c.f.u.) on a Luria-Bertani (LB) agar plate—after 24 h incubation at 37° C.—and calculating the c.f.u. per milliliter of the liquid culture (c.f.u./ml).

Triafluocyl stock solution of 100 mg/ml is prepared by adding to 50 mg Triaflyocyl vial, provided by Cayman Chemical, 500 µl of DMSO (Sigma-Aldrich Merk, Item No. D2650). Following dissolution in DMSO Triafluocyl is further diluted in DMSO to 20 mg/ml working solution. Both the stock and working solution are stored at −20° C. $C_{12(\omega 7)}K\beta_{12}$ stock solution of 10 mg/ml is prepared by adding to 14.3 mg $C12_{(\omega 7)}K\beta_{12}$ dried powder, provided by biomers.net, 1.43 ml of water (Thermo Fisher Item No. AM9930) and stored at −20° C. In both graphs of FIG. 13 $C_{12(\omega 7)}K\beta_{12}$ is referred as OAK.

A single colony of *Escherichia coli* grown on a Luria-Bertani (LB) agar plate is resuspended and cultured in LB medium overnight (O/N) in aerobic conditions (37° C. with 220 rpm shaking in the New Brunswick Innova 4330 Shaker incubator). An aliquot of 100 µl such overnight *Escherichia coli* culture is diluted 1:50 in 5 ml Mueller-Hintom broth (MHB) and is incubated in aerobic conditions during 1 hour 30 minutes (OD=0.08-0.1) to reach the exponential phase of their growth curve. An inoculum of the exponentially growing *Escherichia coli*, corresponding to around $1 \times 10^6$ c.f.u./ml is then incubated in presence or absence of different concentrations of Triafluocyl in 2% DMSO with or without OAK for 24 hr in aerobic conditions (37° C. with 220 rpm shaking in the New Brunswick Innova 4330 Shaker incubator). Growth of *Escherichia coli* in each condition depicted in FIG. 13A is evaluated by reading the Optical Density of each culture at 600 nm ($OD_{600}$) in a spectrophotometer (Victor-3, Perkin Elmer).

The MIC for Triafluocyl in presence of 5 µg/ml OAK against *Escherichia coli* (ATCC 8739) is equal to 5 µg/ml. Triafluocyl taken alone at a concentration of 10 µg/ml or OAK alone at a concentration up to 10 µg/ml are unable to inhibit *Escherichia coli* growth (FIG. 13A).

The Minimal Bactericidal Concentration (MBC) of Triafluocyl in presence of 5 µg/ml OAK against *Escherichia coli* (ATCC 8739) is equal to 10 µg/ml (FIG. 13B). To determine the MBC, 20 µl of a dilution 1:100,000 in 0.9% NaCl of cultures with ΔOD=0.2 or 20 µl of a dilution 1:10 in 0.9% NaCl of cultures with ΔOD=0 are spread on LB agar plates to evaluate the number of colony forming unit (c.f.u.) after 24 hr incubation at 37° C.

Example 17

Fluometacyl Antibacterial Effects on *Escherichia coli* (ATCC 8739)

(together with a Oligo-Acyl-Lysine (OAK) as membrane penetrating agent: the $C_{12(\omega 7)}K\beta_{12}$, also called cis-7-dodecenoyl-lysyl-lysyl-aminododecanoyl-lysyl-amide)

Determination of Minimal Inhibitory Concentration (MIC) and Minimal Bactericidal Concentration (MBC) of Fluometacyl (prepared according to WO 99/05143) in presence of $C_{12(\omega 7)}K\beta_{12}$ (purchased from biomers.net, Germany) against *Escherichia coli* (ATCC 8739). The $C_{12(\omega 7)}K\beta_{12}$ was synthesized by solid-phase method as described by I. Radzishevsky in Antimicrobial Agents and Chemotherapy, May 2007 (1753-1759) (https://aac.asm.org/content/51/5/1753).

The Minimal Inhibitory Concentration (MIC) represents the concentration, in a liquid culture, at which there is no visible growth of bacteria after 24 hours incubation (no pellet or cloudiness), i.e. ΔOD at 600 nm equal to zero, wherein ΔOD is the difference between the resulting optical density (OD) with Fluometacyl together with $C_{12(\omega 7)}K\beta_{12}$, and the optical density (OD) of the blank (blank being the medium alone).

The Minimal Bactericidal Concentration (MBC) represents the lowest concentration of Fluometacyl together with $C_{12(\omega7)}K\beta_{12}$ required to kill over a period of 24 hours, at least 99.9% of bacteria present at time zero in a liquid culture. Viable count in the liquid culture is estimated by counting the colony forming units (c.f.u.) on a Luria-Bertani (LB) agar plate—after 24 h incubation at 37° C.—and calculating the c.f.u. per milliliter of the liquid culture (c.f.u./ml).

Fluometacyl stock solution of 20 mg/ml is prepared by adding 250 µl DMSO (Sigma-Aldrich Merk, Item No. D2650) to 5 mg Fluometacyl powder. The stock solution is stored at −20° C.

$C_{12(\omega7)}K\beta_{12}$ stock solution of 10 mg/ml is prepared by adding to 14.3 mg $C_{12(\omega7)}K\beta_{12}$ dried powder, provided by biomers.net, 1.43 ml of water (Thermo Fisher Item No. AM9930) and stored at −20° C. In both graphs of FIG. 14 $C_{12(\omega7)}K\beta_{12}$ is referred as OAK.

A single colony of *Escherichia coli* grown on a Luria-Bertani (LB) agar plate is resuspended and cultured in LB medium overnight (O/N) in aerobic conditions (37° C. with 220 rpm shaking in the New Brunswick Innova 4330 Shaker incubator). An aliquot of 100 µl such overnight *Escherichia coli* culture is diluted 1:50 in 5 ml Mueller-Hintom broth (MHB) and is incubated in aerobic conditions during 1 hour 30 minutes (OD=0.08-0.1) to reach the exponential phase of their growth curve. An inoculum of the exponentially growing *Escherichia coli*, corresponding to around $1 \times 10^6$ c.f.u./ml is then incubated in presence or absence of different concentrations of Fluometacyl in 2% DMSO with or without OAK for 24 hr in aerobic conditions (37° C. with 220 rpm shaking in the New Brunswick Innova 4330 Shaker incubator). Growth of *Escherichia coli* in each condition depicted in FIG. 14A is evaluated by reading the Optical Density of each culture at 600 nm ($OD_{600}$) in a spectrophotometer (Victor-3, Perkin Elmer).

The MIC for Fluometacyl in presence of 5 µg/ml OAK against *Escherichia coli* (ATCC 8739) is equal to 5 µg/ml. Fluometacyl taken alone at a concentration of 10 µg/ml or OAK alone at a concentration up to 10 µg/ml is unable to inhibit *E. coli* growth (FIG. 14A).

The Minimal Bactericidal Concentration (MBC) of Fluometacyl in presence of 5 µg/ml OAK against *Escherichia coli* (ATCC 8739) is equal to 5 µg/ml (FIG. 14B). To determine the MBC, 20 µl of a dilution 1:100,000 in 0.9% NaCl of cultures with ΔOD=0.2 or 20 µl of a dilution 1:10 in 0.9% NaCl of cultures with ΔOD=0 are spread on LB agar plates to evaluate the number of colony forming unit (c.f.u.) after 24 hr incubation at 37° C.

Example 18

Triafluocyl Antibacterial Effects on *Pseudomonas aeruginosa* (ATCC 27853)

(together with a Oligo-Acyl-Lysine (OAK) as membrane penetrating agent: the $C_{12(\omega7)}K\beta_{12}$, also called cis-7-dodecenoyl-lysyl-lysyl-aminododecanoyl-lysyl-amide). The $C_{12(\omega7)}K\beta_{12}$ was synthesized by solid-phase method as described by I. Radzishevsky in Antimicrobial Agents and Chemotherapy, May 2007 (1753-1759) (https://aac.asm.org/content/51/5/1753).

Determination of Minimal Inhibitory Concentration (MIC) of Triafluocyl (Cayman Chemical, Item No. 15425) in presence of $C_{12(\omega7)}K\beta_{12}$ (provided by Custom synthesis Biomers Germany) against *Pseudomonas aeruginosa* (ATCC 27853).

The Minimal Inhibitory Concentration (MIC) represents the concentration, in a liquid culture, at which there is no visible growth of bacteria after 24 hours incubation (no pellet or cloudiness), i.e. ΔOD at 600 nm equal to zero wherein ΔOD is the difference between the resulting optical density (OD) with the molecule together with $C_{12(\omega7)}K\beta_{12}$, and the optical density (OD) of the blank (blank is the medium alone).

Triafluocyl stock solution of 100 mg/ml is prepared by adding to 50 mg Triaflyocyl vial, provided by Cayman Chemical, 500 µl of DMSO (Sigma-Aldrich Merk, Item No. D2650). Following dissolution in DMSO, Triafluocyl is further diluted in DMSO to 20 mg/ml working solution. Both the stock and working solution are stored at −20° C.

$C_{12(\omega7)}K\beta_{12}$ stock solution is prepared in water at 10 mg/ml and stored at −20° C. In FIG. 15A, $C_{12(\omega7)}K\beta_{12}$ is referred as OAK.

A single colony of *Pseudomonas aeruginosa* grown on a Tryptic Soy agar (TSA) plate is resuspended and cultured in Tryptic Soy Broth (TSB) medium overnight (O/N) in aerobic conditions (37° C. with 190 rpm shaking in New Brunswick Innova 4200 Incubator Shaker). Next day the resulting inoculum is diluted again at 1:100 in Mueller-Hinton broth (MHB) and then incubated in aerobic conditions for 1 h30 (OD=0.08-0.1) to reach an exponential phase in the grown curve. A resulting inoculum corresponding to around $5 \times 10^5$ colony forming unit (CFU)/ml, is further incubated in presence or absence of different concentrations (10 and 20 µg/ml) of Triafluocyl in 2% DMSO with or without $C_{12(\omega7)}K\beta_{12}$ for 18 hr in aerobic conditions (37° C. with 190 rpm shaking in New Brunswick Innova 4200 Incubator Shaker). Growth of *Pseudomonas aeruginosa* in each condition depicted in FIG. 15A is evaluated by reading the OD of each culture at 600 nm ($OD_{600}$) in a spectrophotometer (Fisher Scientific, cell density meter model 40).

The MIC for Triafluocyl in presence of 10 µg/ml OAK against *Pseudomonas aeruginosa* (ATCC 27853) is equal to 10 µg/ml. Triafluocyl taken alone at a concentration of 10 µg/ml or OAK alone at a concentration up to 10 µg/ml are unable to inhibit *P. aeruginosa* growth (FIG. 15A).

Example 19

Fluometacyl Antibacterial Effects on *Pseudomonas aeruginosa* (ATCC 27853)

(together with a Oligo-Acyl-Lysine (OAK) as membrane penetrating agent: the $C_{12(\omega7)}K\beta_{12}$, also called cis-7-dodecenoyl-lysyl-lysyl-aminododecanoyl-lysyl-amide)

Determination of Minimal Inhibitory Concentration (MIC) of Fluometacyl (prepared according to WO99/0514) in presence of $C_{12(\omega7)}K\beta_{12}$ (provided by Biomers.net Germany) against *Pseudomonas aeruginosa* (ATCC 27853). The $C_{12(\omega7)}K\beta_{12}$ was synthesized by solid-phase method as described by I. Radzishevsky in Antimicrobial Agents and Chemotherapy, May 2007 (1753-1759) (https://aac.asm.org/content/51/5/1753)

The Minimal Inhibitory Concentration (MIC) represents the concentration, in a liquid culture, at which there is no visible growth of bacteria after 24 hours incubation (no pellet or cloudiness), i.e. ΔOD at 600 nm equal to zero wherein ΔOD is the difference between the resulting optical density (OD) with the molecule together with $C_{12(\omega7)}K\beta_{12}$, and the optical density (OD) of the blank (blank is the medium alone).

Fluometacyl stock solution of 20 mg/ml is prepared by adding 250 µl DMSO (Sigma-Aldrich Merk, Item No. D2650) to 5 mg Fluometacyl powder. The stock solution is stored at −20° C.

$C_{12(\omega7)}K\beta_{12}$ stock solution is prepared in water at 10 mg/ml and stored at −20° C. In FIG. 16A, $C_{12(\omega7)}K\beta_{12}$ is referred as OAK.

A single colony of Pseudomonas aeruginosa grown on a Tryptic Soy agar (TSA) plate is resuspended and cultured in Tryptic Soy Broth (TSB) medium overnight (O/N) in aerobic conditions (37° C. with 220 rpm shaking in New Brunswick Innova 4200 Incubator Shaker). Next day the resulting inoculum is diluted again at 1:100 in Mueller-Hinton broth (MHB) and then incubated in aerobic conditions for 1 h30 (OD=0.08-0.1) to reach an exponential phase in the grown curve. A resulting inoculum corresponding to around $5\times10^5$ colony forming unit (CFU)/ml, is further incubated in presence or absence of different concentrations (10 and 20 μg/ml) of Fluometacyl in 2% DMSO with or without $C_{12(\omega7)}K\beta_{12}$ for 18 hr in aerobic conditions (37° C. with 190 rpm shaking in New Brunswick Innova 4200 Incubator Shaker). Growth of Pseudomonas aeruginosa in each condition depicted in FIG. 16A is evaluated by reading the Optical Density of each culture at 600 nm ($OD_{600}$) in a spectrophotometer (Fisher Scientific, cell density meter model 40).

The MIC for Fluometacyl in presence of 10 μg/ml $C_{12(\omega7)}K\beta_{12}$ against Pseudomonas aeruginosa (ATCC 27853) is equal to 20 μg/ml. Fluometacyl taken alone at a concentration of 20 μg/ml or C12(ω7)Kβ12 alone at a concentration up to 10 μg/ml are unable to inhibit P. aeruginosa growth (FIG. 16A).

What is claimed is:

1. A method for treatment of a bacterial infection in a host mammal in need of such treatment comprising administering to the host mammal an effective amount of a Triazolo(4,5-d)pyrimidine of formula (1):

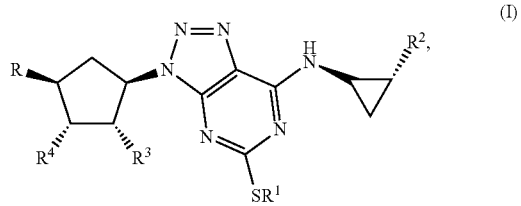

(I)

wherein $R^1$ is $C_{3-5}$ alkyl optionally substituted by one or more halogen atoms; $R^2$ is a phenyl group, optionally substituted by one or more halogen atoms; $R^3$ and $R^4$ are both hydroxyl; R is XOH, wherein X is $CH_2$, or a bond, and wherein when X is a bond, R is OH;

or a pharmaceutical acceptable salt, provided that when X is $CH_2$ or a bond, $R^1$ is not propyl; when X is $CH_2$ and $R^1$ is $CH_2CH_2CF_3$, butyl or pentyl, the phenyl group at $R^2$ must be substituted by fluorine.

2. The method according to claim 1 wherein $R^2$ is phenyl substituted by fluorine atoms.

3. The method according to claim 1, wherein R is OH.

4. The method according to claim 1, wherein the Triazolo (4,5-d)pyrimidine of formula (1) is selected from the group consisting of:
   (1R-(1α, 2α, 3β(1R*, 2*),5β))-3-(7-((2-(3,4-difluorophenyl)cyclopropyl)amino)-5-((3,3,3-trifluoropropyl)thio) 3H-1,2,3-triazolo(4,5d)pyrimidin-3-yl)5(hydroxy)cyclopentane-1,2-diol;
   (1S,2R,3S,4R)-4-[7-[[(1R,2S)-2-(3,4-Difluorophenyl)cyclopropyl]amino]-5-(propylthio)-3H-1,2,3-triazolo[4, 5-d]pyrimidin-3-y]-1,2-3cyclopentanetriol; and
   a pharmaceutical acceptable salt.

5. The method according to claim 1, wherein the Triazolo (4,5-d)pyrimidine of formula (1) is (1S,2R,3 S,4R)-4-[7-[[(1R,2S)-2-(3,4-Difluorophenyl)cyclopropyl]amino]-5-(propylthio)-3H-1,2,3-triazolo[4,5-d]pyrimidin-3-yl]-1,2,3-cyclopentanetriol, also called Fluometacyl.

6. The method according to claim 1, wherein the effective amount to be administered to the host mammal is less than 1.8 g per day.

7. A method of killing bacteria or reducing bacterial growth in a biofilm formation comprising applying on a surface an effective amount of a Triazolo(4,5-d)pyrimidine of formula (1):

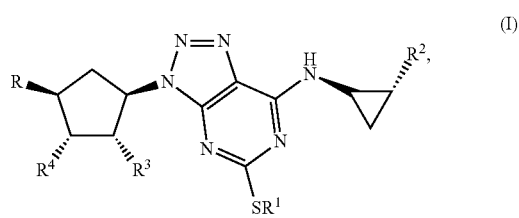

(I)

wherein $R^1$ is $C_{3-5}$ alkyl optionally substituted by one or more halogen atoms; $R^2$ is a phenyl group, optionally substituted by one or more halogen atoms; $R^3$ and $R^4$ are both hydroxyl; R is XOH, wherein X is $CH_2$, $OCH_2CH_2$, or a bond, and wherein when X is a bond, R is OH;

or a pharmaceutical acceptable salt, provided that when X is $CH_2$ or a bond, $R^1$ is not propyl; when X is $CH_2$ and $R^1$ is $CH_2CH_2CF_3$, butyl or pentyl, the phenyl group at $R^2$ must be substituted by fluorine; when X is $OCH_2CH_2$ and $R^1$ is propyl, the phenyl group at $R^2$ must be substituted by fluorine.

8. The method according to claim 7 wherein $R^2$ is phenyl substituted by fluorine atoms.

9. The method according to claim 7, wherein R is OH or $OCH_2CH_2OH$.

10. The method according to claim 7, wherein R is OH.

11. The method according to claim 7, wherein the Triazolo (4,5-d)pyrimidine derivative of formula (1) is selected from the group consisting of:
   (1R-(1α, 2α, 3β(1R*, 2*),5β))-3-(7-((2-(3,4-difluorophenyl)cyclopropyl)amino)-5-((3,3,3-trifluoropropyl)thio) 3H-1,2,3-triazolo(4,5d)pyrimidin-3-yl)5(hydroxy)cyclopentane-1,2-diol;
   (1S-(1α, 2α, 3β(1R*, 2*),5β))-3-(7-((2-(3,4-difluorophenyl)cyclopropyl)amino)-5-(propylthio)-3H-1,2,3-triazolo(4,5d)pyrimidin-3-yl)5(2-hydroxyethoxy)cyclopentane-1,2-diol;
   (1S,2S,3R,5S)-3-[7-[[(1R,2S)-2-(3,4-difluorophenyl)cyclopropylamino]-5-(propylthio)-3H-[1,2,3]-triazolo[4, 5-d]pyrimidin-3-yl]-5-(2-hydroxyethoxy)-1,2-cyclopentanediol;
   (1S,2S,3R,5S)-3-[7-[1R,2S)-2-(4-fluorophenyl)cyclopropylamino]-5-(propylthio)-3H-[1,2,3]-triazolo[4,5-d] pyrimidin-3-yl]-5-(2-hydroxyethoxy)-1,2-cyclopentanediol;
   (1S,2R,3S,4R)-4-[7-[[(1R,2S)-2-(3,4-Difluorophenyl)cyclopropyl]amino]-5-(propylthio)-3H-1,2,3-triazolo[4, 5-d]pyrimidin-3-y]-1,2-3 cyclopentanetriol; and
   a pharmaceutical acceptable salt.

12. The method according to claim 7, wherein the Triazolo(4,5-d)pyrimidine derivative of formula (1) is (1S,2S, 3R,5S)-3-[7-[(1R,2S)-2-(3,4-difluorophenyl)cyclopropylamino]-5-(propylthio)-3H-[1,2,3]-triazolo[4,5-d]pyrimidin-3-yl]-5-(2-hydroxyethoxy)-1,2-cyclopentanediol, also called Triafluocyl.

13. The method according to claim 7, wherein the Triazolo(4,5-d)pyrimidine of formula (1) is (1S,2R,3S,4R)-4-[7-[[(1R,2S)-2-(3,4-Difluorophenyl)cyclopropyl]amino]-5-(propylthio)-3H-1,2,3-triazolo[4,5-d]pyrimidin-3-yl]-1,2,3-cyclopentanetriol, also called Fluometacyl.

14. The method according to claim 7, wherein the effective amount is between 0.1 and 1000 µg/ml.

15. The method according to claim 7, wherein the surface is located on a medical device.

16. The method according to claim 7 wherein the surface is located on a biomaterial.

17. The method according to claim 15, wherein the medical device is a heart valve.

18. The method according to claim 15, wherein the medical device is a catheter.

19. A method of reducing risk of acquiring a bacterial infection in a host mammal comprising administering to the host mammal an effective amount of a Triazolo(4,5-d)pyrimidine of formula (1):

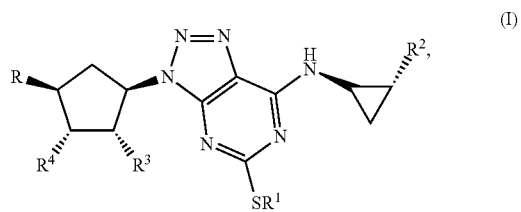

(I)

wherein $R^1$ is $C_{3-5}$ alkyl optionally substituted by one or more halogen atoms; $R^2$ is a phenyl group, optionally substituted by one or more halogen atoms; $R^3$ and $R^4$ are both hydroxyl; R is XOH, wherein X is $CH_2$ or a bond, and wherein when X is a bond, R is OH;

or a pharmaceutical acceptable salt, provided that when X is $CH_2$ or a bond, $R^1$ is not propyl; when X is $CH_2$ and $R^1$ is $CH_2CH_2CF_3$, butyl or pentyl, the phenyl group at $R^2$ must be substituted by fluorine.

20. The method according to claim 19 wherein the Triazolo(4,5-d)pyrimidine of formula (1) is (1S,2R,3S,4R)-4-[7-[[(1R,2S)-2-(3,4-Difluorophenyl)cyclopropyl]amino]-5-(propylthio)-3H-1,2,3-triazolo[4,5-d]pyrimidin-3-yl]-1,2,3-cyclopentanetriol, also called Fluometacyl.

* * * * *

UNITED STATES PATENT AND TRADEMARK OFFICE
CERTIFICATE OF CORRECTION

PATENT NO. : 10,905,691 B2
APPLICATION NO. : 16/688961
DATED : February 2, 2021
INVENTOR(S) : Oury et al.

Page 1 of 5

It is certified that error appears in the above-identified patent and that said Letters Patent is hereby corrected as shown below:

On the Title Page

In Column 2, item (56), Other Publications, Line 13, delete "Angimicrobial" and insert -- Antimicrobial --.

In Column 2, item (57), Abstract, Line 4, delete "formula(I):" and insert -- formula (I): --.

In the Drawings

In sheet 3 of 17, FIG. 3, Graph A3, Line 3 (approx.), delete "Triafluocy" and insert -- Triafluocyl --.

In sheet 3 of 17, FIG. 3, Graph A4, Line 3 (approx.), delete "Triafluocy" and insert -- Triafluocyl --.

In sheet 10 of 17, FIG. 8 (continued), Line 2 (approx.), delete "E.faecalis" and insert -- E. faecalis --.

In sheet 11 of 17, FIG. 10, Graph B, Line 1, delete "S.epidermidis" and insert -- S. epidermidis --.

In sheet 16 of 17, FIG. 15, Line 13 (approx.), delete "Figure" and insert -- FIG. --.

In the Specification

In Column 1, Line 33, delete "2014" and insert -- 2014. --.

In Column 3, Line 31, delete "[ICDs])" and insert -- [ICDs] --.

In Column 5, Line 46, delete "Helocobacter" and insert -- Helicobacter --.

In Column 6, Line 7 (approx.), delete "(OAKS)" and insert -- (OAKs) --.

In Column 6, Line 14, delete "(VII)." and insert -- (VI). --.

Signed and Sealed this
Fourteenth Day of June, 2022

Katherine Kelly Vidal
*Director of the United States Patent and Trademark Office*

CERTIFICATE OF CORRECTION (continued)
U.S. Pat. No. 10,905,691 B2

In Column 8, Line 45, delete "(OAKS)" and insert -- (OAKs) --.

In Columns 7 and 8, Line 67 (approx.), delete "OAK C12(▢)7X" and insert -- OAK C12 (ω7)X --.

In Columns 9 and 10, Line 20 (approx.), delete "$NH_3^+$," and insert -- $NH_3^+$ --.

In Column 9, Line 26, delete "cardioverter" and insert -- cardioverter. --.

In Column 9, Lines 34-35, delete "formula(I):" and insert -- formula (I): --.

In Column 9, Line 64, delete "(IR-" and insert -- (1R- --.

In Column 9, Line 66, delete "pyrimidin-3 yl)" and insert -- pyrimidin-3-yl) --.

In Column 10, Line 34, delete "3-y]" and insert -- 3-yl] --.

In Column 10, Line 34, delete "3cyclopentanetriol;" and insert -- 3-cyclopentanetriol; --.

In Column 10, Line 41, delete "(1R," and insert -- (1S, --.

In Column 10, Line 65, delete "R3" and insert -- $R_3$ --.

In Column 10, Line 65, delete "R4" and insert -- $R_4$ --.

In Column 11, Line 13, delete "(IR-" and insert -- (1R- --.

In Column 11, Line 15 (approx.), delete "pyrimidin-3 yl)" and insert -- pyrimidin-3-yl) --.

In Column 11, Line 31, delete "3-y]" and insert -- 3-yl] --.

In Column 11, Line 31, delete "3cyclopentanetriol;" and insert -- 3-cyclopentanetriol; --.

In Column 11, Line 53, delete "formula(I):" and insert -- formula (I): --.

In Column 11, Line 67, delete "R3" and insert -- $R_3$ --.

In Column 11, Line 67, delete "R4" and insert -- $R_4$ --.

In Column 12, Line 59, delete "R1" and insert -- $R_1$ --.

In Column 12, Line 59, delete "C3" and insert -- $C_3$ --.

In Column 13, Line 13 (approx.), delete "CH2" and insert -- $CH_2$ --.

In Column 13, Line 17 (approx.), delete "R2" and insert -- $R_2$ --.

CERTIFICATE OF CORRECTION (continued)
U.S. Pat. No. 10,905,691 B2

In Column 13, Line 18, delete "and or" and insert -- and/or --.

In Column 13, Line 38, delete "CH2" and insert -- $CH_2$ --.

In Column 13, Line 39, delete "3,4 difluorophenyl." and insert -- 3,4-difluorophenyl. --.

In Column 13, Line 46, delete "(3H" and insert -- 3H --.

In Column 13, Lines 65-66, delete "cyclopentanediol)" and insert -- cyclopentanediol --.

In Column 15, Line 33, delete "(3H" and insert -- 3H --.

In Column 15, Lines 38-39, delete "cyclopentanediol);" and insert -- cyclopentanediol; --.

In Column 15, Line 43, delete "cyclopentanediol)" and insert -- cyclopentanediol --.

In Column 15, Line 57, delete "(3H" and insert -- 3H --.

In Column 15, Lines 62-63, delete "cyclopentanediol);" and insert -- cyclopentanediol; --.

In Column 15, Lines 66-67, delete "cyclopentanediol);" and insert -- cyclopentanediol; --.

In Column 16, Line 6, delete "cyclopentanediol)" and insert -- cyclopentanediol --.

In Column 16, Line 42, delete "pyrolitic" and insert -- pyrolytic --.

In Column 16, Line 45 (approx.), delete "pericardium" and insert -- pericardium. --.

In Column 17, Line 42, delete "24h" and insert -- 24 h --.

In Column 17, Line 46, delete "Mynocycline:" and insert -- Minocycline: --.

In Column 17, Line 47, delete "methilcillin" and insert -- methicillin --.

In Column 17, Line 60, delete "polymixin" and insert -- polymyxin --.

In Column 18, Line 1, delete "polymixin" and insert -- polymyxin --.

In Column 19, Line 7, delete "FIG. 1" and insert -- FIG. 1, --.

In Column 19, Line 22, delete "cyclopentanediol)" and insert -- cyclopentanediol --.

In Column 19, Line 35, delete "glucose" and insert -- glucose. --.

In Column 19, Line 57, delete "cyclopentanediol)" and insert -- cyclopentanediol --.

CERTIFICATE OF CORRECTION (continued)
U.S. Pat. No. 10,905,691 B2

In Column 20, Line 5, delete "FIG. 3" and insert -- FIG. 3, --.

In Column 20, Line 30, delete "glucose" and insert -- glucose. --.

In Column 23, Line 10 (approx.), delete "methilcillin" and insert -- methicillin --.

In Column 23, Line 33, delete "methilcillin" and insert -- methicillin --.

In Column 23, Line 50, delete "methilcillin" and insert -- methicillin --.

In Column 23, Line 54, delete "methilcillin" and insert -- methicillin --.

In Column 24, Line 37, delete "24h" and insert -- 24 h --.

In Column 25, Line 27, delete "methilcillin" and insert -- methicillin --.

In Column 26, Line 2, delete "Minocyclin" and insert -- Minocycline --.

In Column 26, Line 4, delete "8B)" and insert -- 8B --.

In Column 27, Table 2, Line 2, "methilcillin" and insert -- methicillin --.

In Column 27, Table 2, Line 3, "Enteroccocus." and insert -- Enterococcus. --.

In Column 27, Line 20, delete "Methilcillin" and insert -- Methicillin --.

In Column 27, Line 36, delete "Staphyloccocus" and insert -- Staphylococcus --.

In Column 27, Line 36, delete "Staphyloccocus" and insert -- Staphylococcus --.

In Column 28, Line 26, delete "1 h30" and insert -- 1 hour 30 minutes --.

In Column 29, Line 11, delete "1 h30" and insert -- 1 hour 30 minutes --.

In Column 29, Line 66, delete "Triaflyocyl" and insert -- Triafluocyl --.

In Column 30, Line 14, delete "Hintom" and insert -- Hinton --.

In Column 30, Line 48, delete "amide)" and insert -- amide). --.

In Column 31, Line 22, delete "Hintom" and insert -- Hinton --.

In Column 32, Line 8, delete "Triaflyocyl" and insert -- Triafluocyl --.

In Column 32, Line 23, delete "1 h30" and insert -- 1 hour 30 minutes --.

CERTIFICATE OF CORRECTION (continued)
U.S. Pat. No. 10,905,691 B2

In Column 32, Line 47, delete "amide)" and insert -- amide). --.

In Column 33, Line 11, delete "1 h30" and insert -- 1 hour 30 minutes --.

In the Claims

In Column 33, Line 34, Claim 1, delete "formula (1)" and insert -- formula (I) --.

In Column 33, Line 58, Claim 4, delete "formula (1)" and insert -- formula (I) --.

In Column 33, Line 66, Claim 4, delete "3-y]" and insert -- 3-yl] --.

In Column 33, Line 66, Claim 4, delete "3cyclopentanetriol;" and insert -- 3-cyclopentanetriol; --.

In Column 34, Line 2, Claim 5, delete "formula (1)" and insert -- formula (I) --.

In Column 34, Line 2, Claim 5, delete "(1S,2R,3 S,4R)" and insert -- (1S,2R,3S,4R) --.

In Column 34, Line 12, Claim 7, delete "formula (1)" and insert -- formula (I) --.

In Column 34, Line 64, Claim 11, delete "3-y]" and insert -- 3-yl] --.

In Column 34, Line 64, Claim 11, delete "3 cyclopentanetriol;" and insert -- 3-cyclopentanetriol; --.